United States Patent
Cabiri et al.

(10) Patent No.: US 10,646,643 B2
(45) Date of Patent: May 12, 2020

(54) NEEDLE INSERTION AND RETRACTION MECHANISM

(71) Applicant: West Pharma. Services IL, Ltd., Ra'anana (IL)

(72) Inventors: Oz Cabiri, Macabim-Reut (IL); Ran Hezkiahu, Herzliya (IL); Tal Hammer, Ramat-Gan (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 0 days.

(21) Appl. No.: 16/071,538

(22) PCT Filed: Dec. 22, 2016

(86) PCT No.: PCT/US2016/068367
§ 371 (c)(1),
(2) Date: Jul. 20, 2018

(87) PCT Pub. No.: WO2017/127215
PCT Pub. Date: Jul. 27, 2017

(65) Prior Publication Data
US 2019/0030240 A1    Jan. 31, 2019

Related U.S. Application Data

(60) Provisional application No. 62/281,536, filed on Jan. 21, 2016.

(30) Foreign Application Priority Data

Oct. 10, 2016    (WO) ................. PCT/US2016/056223
Oct. 10, 2016    (WO) ................. PCT/US2016/056238
Oct. 10, 2016    (WO) ................. PCT/US2016/056247

(51) Int. Cl.
*A61M 5/142*    (2006.01)
*A61M 5/145*    (2006.01)
(Continued)

(52) U.S. Cl.
CPC ....... *A61M 5/14248* (2013.01); *A61M 5/1452* (2013.01); *A61M 2005/14256* (2013.01); *A61M 2005/1585* (2013.01); *A61M 2005/206* (2013.01)

(58) Field of Classification Search
CPC .... A61M 5/14248–2005/1426; A61M 5/1452; A61M 2005/1585;
(Continued)

(56) References Cited

U.S. PATENT DOCUMENTS 1,125,887 A    1/1915   Schimmel
1,321,550 A   11/1919   Platt
(Continued)

FOREIGN PATENT DOCUMENTS

CN    1863566 A    11/2006

OTHER PUBLICATIONS

Int'l Search Report and Written Opinion dated Apr. 21, 2017 in Int'l Application No. PCT/US2016/068367.
(Continued)

*Primary Examiner* — Bhisma Metha
*Assistant Examiner* — Laura C Schell
(74) *Attorney, Agent, or Firm* — Panitch Schwarze Belisario & Nadel LLP

(57) ABSTRACT

A system and method are provided for preventing a sharp stick hazard from a needle tip of an automatic injector device. In some embodiments, a skin contact surface of the device is attached to an injection site, for example by an adhesive. Optionally a locking mechanism holds a needle extended into an injection site. A body of the device is optionally movably attached to the skin contact surface. Pulling the body away from the injection site optionally moves the body with respect to the skin contact surface. Movement of the body with respect to the skin contact
(Continued)

surface optionally moves interlinked parts of the locking mechanism, releasing the locking mechanism.

13 Claims, 22 Drawing Sheets

(51) Int. Cl.
 *A61M 5/158* (2006.01)
 *A61M 5/20* (2006.01)
(58) Field of Classification Search
 CPC ........ A61M 2005/1586; A61M 5/1626; A61M 2005/206; A61M 2005/2073
 See application file for complete search history.

(56) References Cited

U.S. PATENT DOCUMENTS

| | | |
|---|---|---|
| 4,710,178 A | 12/1987 | Henri et al. |
| 5,858,001 A | 1/1999 | Tsals et al. |
| 6,186,979 B1 | 2/2001 | Dysarz |
| 6,189,292 B1 | 2/2001 | Odell et al. |
| 6,500,150 B1 | 12/2002 | Gross et al. |
| 6,824,529 B2 | 11/2004 | Gross et al. |
| 6,843,782 B2 | 1/2005 | Gross et al. |
| 7,967,795 B1 | 6/2011 | Cabiri |
| 8,496,862 B2 | 7/2013 | Zelkovich et al. |
| 8,603,028 B2 | 12/2013 | Mudd et al. |
| 8,721,603 B2 | 5/2014 | Lundquist |
| 9,149,575 B2 | 10/2015 | Cabiri |
| 2005/0065466 A1* | 3/2005 | Vedrine ............. A61M 5/14248 604/93.01 |
| 2009/0093792 A1 | 4/2009 | Gross et al. |
| 2013/0131589 A1 | 5/2013 | Mudd et al. |
| 2013/0253434 A1 | 9/2013 | Cabiri |
| 2014/0163526 A1 | 6/2014 | Cabiri et al. |
| 2015/0112278 A1 | 4/2015 | Ray et al. |
| 2015/0157806 A1 | 6/2015 | Knutsson |

OTHER PUBLICATIONS

Int'l Preliminary Report on Patentability dated Nov. 30, 2017 in Int'l Application No. PCT/US2016/068367.

* cited by examiner

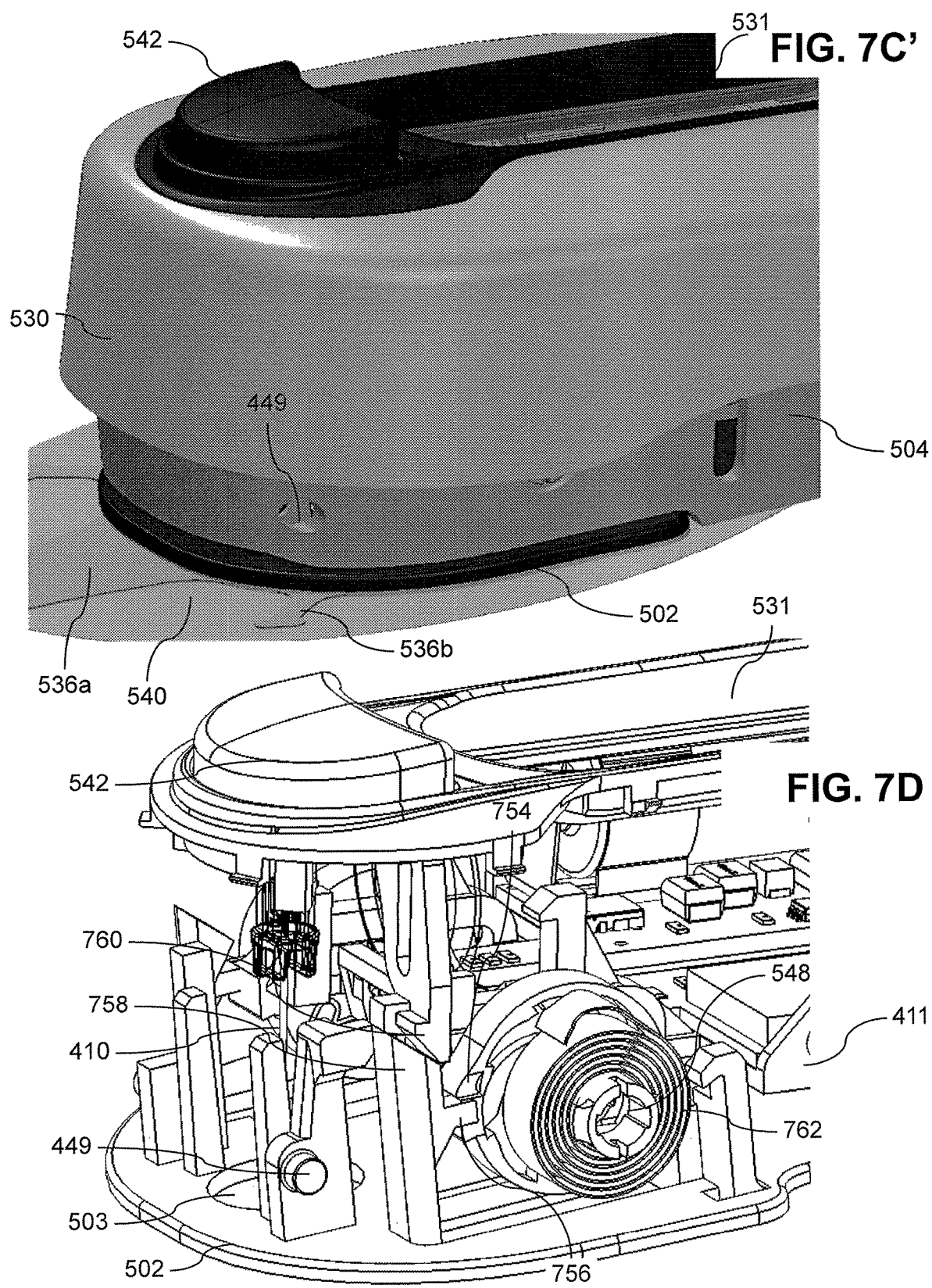

NEEDLE INSERTION AND RETRACTION MECHANISM

RELATED APPLICATION/S

This application is a section 371 of International Application No. PCT/US16/68367, filed Dec. 22, 2016, which was published in the English language on Jul. 27, 2017 under International Publication No. WO 2017/127215 A1, which claims priority to International Application No. PCT/US16/56223, filed Oct. 10, 2016, International Application No. PCT/US16/56238, filed Oct. 10, 2016, International Application No. PCT/US16/56247, filed on Oct. 10, 2016, all of which claim the benefit of U.S. Provisional Application No. 62/281,536, filed Jan. 21, 2016, the disclosures of which are incorporated herein by reference.

FIELD AND BACKGROUND OF THE INVENTION

The present invention, in some embodiments thereof, relates to a system for extending and/or protecting a needle and particularly, but not exclusively, to a system to automatically retract a needle of an auto-injector when the injector is removed from an injection site.

U.S. Pat. No. 9,149,575 apparently discloses, "An apparatus (110) includes an activation mechanism (20) and a safety latch (122). The activation mechanism is operative to deploy a needle (116) to protrude out of a housing (112), the needle (116) having a longitudinal axis. The safety latch (122) is movably mounted on the housing (112) and formed with a needle opening (129) to allow the needle (116) to pass therethrough. The safety latch (122) has a first position wherein the needle (116) is aligned to pass through the needle opening (129) and a second position wherein the safety latch (122) is moved with respect to the housing (112) such that the needle (116) is blocked from movement in a direction parallel to the longitudinal axis thereof by a portion of the safety latch (122) distanced from the needle opening (129)."

U.S. Pat. No. 7,530,964 apparently discloses, "A needle device has a needle retraction mechanism that retracts the needle upon removing the device from the skin surface (either intentionally or unintentionally). Once the needle is retracted, the device is rendered inoperative. The needle can be further made inoperative by bending it when one attempts to reuse the device. In another embodiment, a needle opening formed in the base of the housing can be covered to render the needle inoperative when one attempts to reuse the device. In another embodiment, the needle device instead has a needle shield that automatically covers the needle after use."

U.S. Pat. Nos. 8,915,882, 6,500,150, 6,824,529, and 6,843,782, apparently disclose a drug delivery device having a base member defining a skin-contacting surface, a syringe serving as a reservoir for the drug, and means for expelling drug from the syringe. The syringe is connected to the base member such that the longitudinal axis of the syringe is substantially parallel to the skin surface. A delivery needle is in communication with the syringe. The needle has an angled bend, which directs the tip of the needle substantially perpendicular to the skin-contacting surface. In use, the tip of the needle is adapted to penetrate the skin of the subject.

For such relatively slow release, an automatic expulsion device has also been suggested. U.S. Pat. No. 5,858,001 discloses a liquid drug delivery device adhered to the skin of a subject by a base member defining a skin-contacting surface having an adhesive coating. A columnar cartridge serves as reservoir for the drug and is incorporated in a housing, which is connected to the base member such that, in use, the longitudinal axis of the cartridge is disposed substantially parallel to the skin-contacting surface. A delivery needle communicating in use with the interior of the cartridge penetrates the skin of the subject when the housing snaps downward relative to the base member. This action also causes the actuation of a citric acid/sodium bicarbonate gas generator, which generates a gas to move a piston within the cartridge, compressing the drug compartment. This compression causes a stopper to be penetrated by a conduit in communication with the delivery needle, allowing the drug to be ejected from the compartment through the needle and into the subcutaneous tissue of the subject.

If using an injector device then the syringe cartridge may be preloaded and needs to be kept sterile during the process of locating it in the injector. U.S. Patent Publication No. 20140163526 discloses an automated injection device, which may be loaded with a standard type syringe and/or hypodermic needle. Optionally the syringe may be preloaded. The syringe may be loaded into the injector in a sterile state with needle cover in place. The injector includes a fastener, such as an adhesive base. The fastener may assist a user to hold the injector steady on the skin of a patient for an extended period. For example, the injector may be used to give injections of volume ranging between 0.5 and 3.0 ml over a time period ranging between 30 seconds and 10 minutes.

U.S. Pat. No. 8,603,028 relates to a "handheld injection device includes a first housing having a first axis and a second housing having a second axis. In one embodiment, the second housing is configured to support a needle. In one embodiment, the first axis and a second axis form an adjustable angle between about 180 degrees and about 90 degrees."

Additional background art includes U.S. Pat. No. 6,189,292. U.S. Patent Publication No. 20130253434, U.S. Patent Publication No. 2009/093,792, U.S. Pat. No. 7,967,795 U.S. Patent Publication No. 20140194854.

SUMMARY OF THE INVENTION

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

According to an aspect of some embodiments of the invention, there is provided a system for shielding a needle as an injection device is removed from an injection site: a base including a contact surface having an adhesive for attachment to an injection zone; a tip of a needle movable between an exposed position on a first side of the contact surface to a shielded position on an opposite side of the shielding surface; a lock inhibiting movement of the tip from the exposed position to the shielded position a body movably attached to the base, movable between a first position and a second position distanced from the first position relative to the contact surface; the body linked to the lock to engage the lock to inhibit the movement of the tip from the exposed position to the shielded position when the body is in the first position and the body disengaging the lock to allow movement of the needle tip for the exposed position to the shielded position.

According to some embodiments of the invention, the in the second position, a center of mass of the body is further from the contact surface than in the first position.

According to some embodiments of the invention, the base is positioned between the contact surface and the body of the injector and wherein the body is movable between the first position near the base and the second position distanced from the base.

According to some embodiments of the invention, the system further includes a biasing member biasing the body toward the second position.

According to some embodiments of the invention, the system further includes a retainer that retrains the body in the first position during drug delivery.

According to some embodiments of the invention, the retainer is configured to release the body to the second position in response to pulling the body away from the contact surface of the base.

According to some embodiments of the invention, the retainer includes a second contact surface and a second adhesive such that when the contact surface of the base is attached to an injection zone and the body is in the first position, the second adhesive retains the body in the first position by adhesion.

According to some embodiments of the invention, the second adhesion surface is flush to the adhesion surface of the base when the body is in the first position such that when the body is in the first position and the contact surface of the base is in contact with an injection site on a skin of a subject, the second contact surface also contacts the skin of the subject.

According to some embodiments of the invention, the body is configured to encourage pulling the body away from the injection surface from a position closer to the second contact surface than to the injection zone.

According to some embodiments of the invention, the system further includes an opening in the base and wherein the needle tip is aligned with the opening such that the needle tip passes through the opening when the needle moves from the exposed position to the shielded position.

According to some embodiments of the invention, the needle is aligned with the opening both when the body is in the first position and when the body is in the second position.

According to some embodiments of the invention, the system further includes a sterile needle cap and wherein the opening is large enough for the sterile needle cap to pass therethrough.

According to some embodiments of the invention, the system further includes a stored energy source and wherein the movement of the needle tip is powered by the stored energy source.

According to some embodiments of the invention, the body is shaped and sized for grasping by a human hand, such that grasping the body and pulling it away from the contact surface causes the moving of the body from the first position to the second position.

According to an aspect of some embodiments of the invention, there, is provided a method of preventing a stick hazard from a needle tip of a drug delivery device, the device including a body, a skin contact surface, a needle and a lock fixing an orientation of the needle tip with respect to the skin contact surface, the lock including interlinked components attached to the body and the skin contact surface, the method including: Adhering the skin contact surface adhered to injection surface with the needle tip locked protruding from the delivery device into the injection surface; Releasing the lock in response to a reorientation of the interlinked components resulting from a movement of the body relative to the skin contact surface while the skin contact surface remains adhered to the injection surface.

According to some embodiments of the invention, the needle tip is biased to retract through an opening in the contact surface, the method further including, retracting the needle tip in response to the unlocking.

According to some embodiments of the invention, the method further includes pulling the body away from the skin contact surface in order to cause the movement.

According to some embodiments of the invention, the body is adhered to the injection surface to inhibit movement of the body away from the skin contact surface further including Overcoming the adhering of the body to the injection surface by means of the pulling.

According to some embodiments of the invention, the method further includes Biasing the body away from the skin contact surface.

According to some embodiments of the invention, the movement of the body relative to the skin contact surface is in a direction away from the skin contact surface.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 7A-7J are perspective and cut away views of various states of an injector in accordance with an embodiment of the present invention;

DESCRIPTION OF SPECIFIC EMBODIMENTS OF THE INVENTION

Figure 1A:
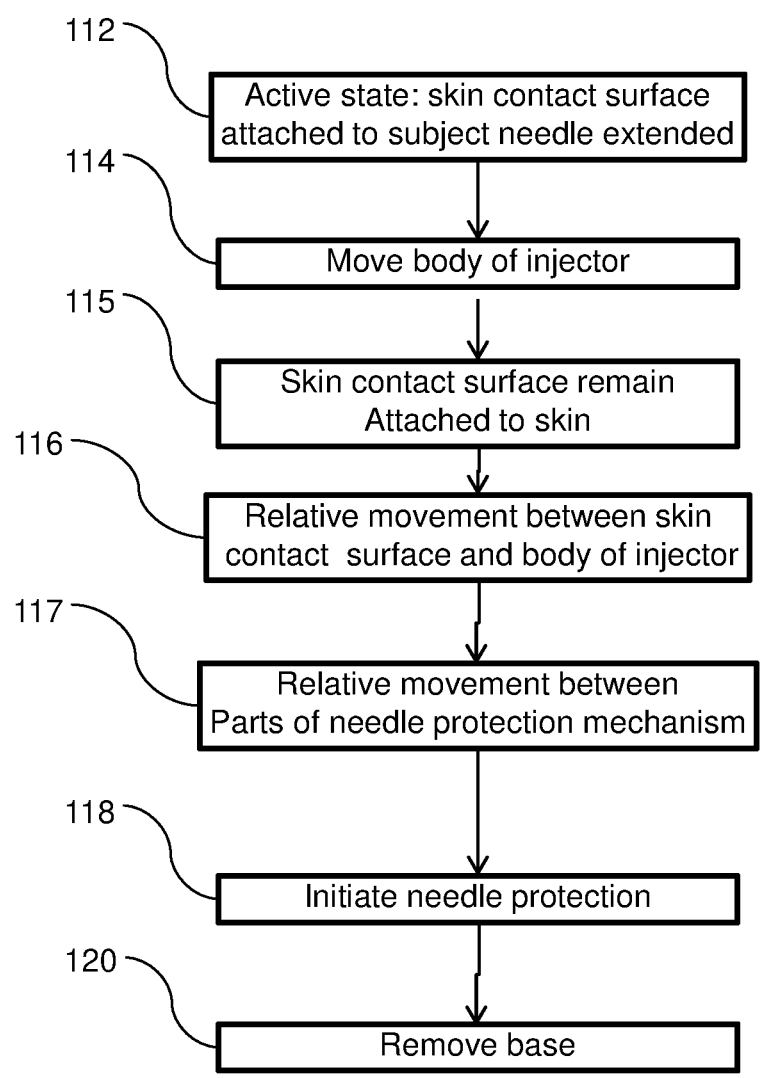
FIG. 1A is a flow chart illustration of a method of protecting a needle in accordance with an embodiment of the present invention.

The present invention, in some embodiments thereof, relates to a system for extending and/or protecting a needle and particularly, but not exclusively, to a system to automatically retract a needle of an auto-injector when the injector is removed from an injection site.

Overview

An aspect of some embodiments of the current invention relates to preventing exposure of a needle of an injector by protecting a needle before a skin contact surface of the injector is removed from an injection surface. For example, a body of the device may be disengaged from the skin contact surface as the device is removed. Disengagement optionally achieves and/or triggers protection of the needle of the injector before the skin contact surface is removed from the injection site.

In some embodiments, an exposed needle is moved to a shielded location when body of the device is moved relative to the injection site and/or a skin contact surface of the device. For example, the body may be moved away from an injection site and or the skin contact surface. For example, the device may include a body (for example including a housing and/or a chassis) that moves with respect to an attachment interface. For example, the body may move from a first location to a second location further away from a contact surface when the shortest distance between the center of mass and the contact surface is larger from the second position than from the first position. For example, the body may move from a first location to a second location further away from an injection site when the shortest distance between the center of mass and point through which the needle tip passes across the contact surface is larger from the second position than from the first position.

An attempt to tamper and/or remove the device from the injection location while a needle tip is exposed optionally causes retraction of the needle into a protected location. For example, the distance of relative movement between the injection site and/or skin contact surface with respect to the body of the device at their closest points may range between 0 to 0.3 mm and/or between 0.3 to 1 mm and/or between 1 mm to 3 mm and/or between 3 mm to 10 mm and/or between 10 mm to 30 mm. Alternatively or additionally, the body may pivot with respect to the injection and/or the skin contact surface to an angle ranging between 0 to 2 degrees and/or between 2 to 6 degrees and/or between 6 to 12 degrees and/or between 12 to 24 degrees and/or between 24 to 45 degrees when the needle retracts. Optionally, the needle may be locked into the protected position. Optionally, movement of the needle to the protected position may be irreversible.

In some embodiments, a sharp hazard may remain covered in many and/or all stages of operation of the device. For example, a needle may be deployed out of a base of a device while the base of the device is attached to an injection site (after the base is connected to the injection site). For example, the needle may be protected while the base remains attached to the injection site (e.g. before the base is removed from the injections site). Optionally, the base may surround the injection site while it is attached thereto. In some embodiments, the base of the device and/or activation may be configured to discourage operation while the base is not connected to the injection site. For example, operation of the device may include placing an adhesive contact surface against an injection site and/or pushing the body of the device toward the contact surface. For example, a user's hesitancy to dirty himself with the adhesive may discourage casual initiation and/or unintentional initiation of the device.

In some embodiments, an injection surface may include a skin surface of a subject. In some embodiments, an injection site may include a site for injecting a pharmaceutical into a subject. Alternatively or additionally, an injection surface may include an artificial surface for demonstrating the device. Alternatively or additionally, an injection surface may include an artificial surface for demonstrating the device.

Alternatively or additionally, an injection surface may include a liquid reservoir in piece of machinery (for example for injecting dye into a printer cartridge).

In some embodiments, a skin sensor and/or contact surface may pivot when an injector is pushed toward an injection site. Optionally, the needle insertion will include pivoting of a cartridge and/or needle assembly. For example, the two pivoting systems may be in opposite directions such that the needle may be oriented at a predetermined angle to the base (for example perpendicular) and/or the angle may be changed when the base is collapsed (for example, due to pushing the device onto the injection site).

Optionally, when the needle is inserted, pivoting of the needle assembly and/or cartridge may partially and/or fully return the needle to the original orientation.

In some embodiments, the base may serve as a proximity and/or skin sensor for stopping and/or protecting the device. For example, when the device is removed from an injection site, the base may be distanced from the body of the injector (for example the housing and/or the chassis and/or the cartridge of the device). Movement of the base with respect to the body of the injector optionally triggers needle protection and/or stops discharge of the drug.

In some embodiments a surface area of a base of the device and/or a skin contact surface thereof and/or an adhesive surface thereof may range between 1 to 5 $cm^2$ and/or 5 to 25 $cm^2$ and/or between 25 to 250 $cm^2$ and/to between 250 to 1000 $cm^2$ and/or between 1000 to 5000 $cm^2$. The base optionally includes between 10 to 70% of the surface area of contact of the device with the skin of a user and/or between 70 to 90% of the surface area of contact of the device with the skin of a user and/or between 90 to 100% of the surface area of contact of the device with the skin of a user.

In some embodiments, a needle opening in base of the device may be large enough to insert and/or remove a sterile needle cover. For example, the width of the opening may range between 1 mm to 2 mm and/or between 2 mm to 4 mm and/or between 4 mm to 10 mm. The cross sectional area of the opening may range for example between 1 to 4 $mm^2$ and/or between 2 to 16 $mm^2$ and/or between 16 to 100 $mm^2$.

In some embodiments, the base of the device is biased towards the body of the device. Alternatively or additionally, the base of the device may be biased away from the body of the device. Optionally, the device may have a retaining mechanism to keep the base from extending away from the body of the device. For example, the retaining mechanism may include an adhesive surface that adheres to the skin of a user and/or keeps the body of the device close to the injection site and/or close to the skin contact surface of the base.

In some embodiments, the force for overcoming the attachment (for example adhesion) of the base to an injection site (for example by pulling the base directly away from the skin surface of a subject) may range of between 0.1 to 1 Newton and/or between 1 to 5 Newtons and/or between 5 to 15 Newtons and/or between 15 to 50 Newtons and/or more. In some embodiments, the force to overcome the retainer that keeps the base close to the body of the device (for example adhesion of the housing to an injection site) for example by pulling the body directly away from the skin surface of a subject may range between 0.1 to 1 Newton and/or between 1 to 5 Newtons and/or between 5 to 15 Newtons.

In some embodiments, a force for overcoming the retainer that keeps the base close to the body (for example adhesion of the housing to an injection site) may be for example between 0.1 to 10% and/or between 10% to 25% and/or between 25 to 75% of the force to overcome the attachment of the base to the injection site. In some embodiments, a force may bias a skin contact surface away from a body and/or a chassis of the injector. For example, the biasing force at the location of greatest movement between the contact surface and the body may range between 0.1 to 0.5 Newton and/or between 0.5 to 2 Newtons and/or between 2 to 5 Newtons and/or between 5 to 10 Newtons.

In some embodiments, a base of an injection device may include an adhesive skirt. For example, the adhesive skirt of the base may extend beyond an area where the adhesive is attached to the base between 1 mm to 5 mm and/or between 10 mm to 50 mm. In some embodiments, a base of an injection device may include an adhesive skirt. In some embodiments, a skin contact area of an injector not on the base may include an adhesive skirt. For example, the adhesive skirt of skin contact area not on the base may extend beyond an area where the adhesive is attached to the injector between 0.1 mm to 1 mm and/or between 1 mm to 5 mm. In some embodiments, the adhesive skirt on the base may extend ranging from 10% to 50% and/or from 50% to 250% and/or from 250% to 1000% or more further than the length to which a skirt extends on another skin contact surface of the injector.

In some embodiments a base in movably mounted to a chassis and/or a housing of the injection device. For example, the base may be pivotally mounted thereto.

Optionally a needle assembly and/or the base are movably mounted to the same component. For example, the needle may be mounted on a pivoting arm and/or plate pivoting from one side of a component (for example a chassis) and/or the base may pivot from an opposite side and/or in an opposite direction. For example, when both the needle and the base are collapsed to the body of the device (e.g. the needle extended through an opening in the base and the base collapsed to the chassis) the relative orientation of the needle to the base may be the same as when the basis and needle plate are moved away from the base (for example the needle is retracted and the base is extended away from the chassis).

An aspect of some embodiments of the current invention relates to performing automated initiation of an injection device and/or protection of a sharp needle by user intuitive actions. In some embodiments, an intuitive user interface allows a user with limited preparation and/or knowledge to operate a device based on untrained assumption and/or actions. Optionally an automated user interface performs actions that might arouse avoidance behavior in an unintuitive manner. Optionally, a user interface operates properly even when a user's untrained assumptions lead him to avoid proper activation of the device and/or lead him to act unpredictably and/or perform acts out of order.

In some embodiments, an injector may be activated by simple intuitive acts. For example, initiation may include placing an easily recognizable skin contact surface (for example a flat surface and/or a surface including an adhesive) onto an injection site and/or pushing the body of the injection device towards the injection site and/or depressing an activation button.

In some embodiments, actions that arouse natural avoidance like needle insertion are not a direct result of an intuitive act. Optionally, needle insertion may not occur as a direct mechanical consequence of the user pushes the body towards the skin. For example, needle insertion may be performed automatically by an actuator system. The actuator may optionally be triggered upon proper placement of the injection device onto the skin and/or upon a command (for example pushing a button) and/or through an automated and/or timed control system.

In some embodiments, a needle is automatically protected when a user pulls an injector away from an injection site.

In some embodiments, activation of an injector may require performance of an ordered series of actions. For example, the device may not be activated by a simple act that may be performed inadvertently. For example, the device may be activated by first removing a protective cap and/or then placing a contact surface against the skin and/or then pushing the device into place on the skin and/or then depressing an activation button. Optionally the device will not be activated by performance of only a portion of the actions and/or performance of actions out of order.

In some embodiments, the system will be insensitive to an actions not part of the proper initiation procedure and/or will be insensitive to an act performed out of the prescribed order. For example, an injector may not be affected (for example not activated and/or not disabled) by engaging of an activation switch before proper placement on the injections site. Alternatively or additionally, some improper actions and/or action performed out of order may block activation of the device.

In some embodiments, an injector device may include a user interface.

Optionally the user interface is designed to encourage intuitive and/or proper use of the injector. For example a status indicator and/or a control (for example an activation button) may be located opposite the skin contact surface such that when the contact surface is against the skin, the user sees and/or can reach the user interface.

Alternatively or additionally, the placement of the user interface may encourage the user to hold the injector in a proper way for example for proper placement and operation of the device.

In some embodiments, a needle extension and/or protection system in accordance with the current invention may be included in a patch injector and/or a stabilized pen injector. For example, a patch injector may include a drug reservoir (for example a syringe) having a longitudinal axis parallel (and/or nearly parallel for example between 1 to 10 degrees and/or 10 to 30 degrees) to a skin contact surface or a base of the injector during drug delivery. Optionally, the long axis of the skin contact surface and/or base of a patch injector may be longer than the height of the injector perpendicular to the skin contact surface. In some embodiments, a skin contact surface of a patch injector and/or stabilized pen injector may include a connector for connecting to an injection site.

For example, a connector may include an adhesive. For example, a stabilized pen injector may include a drug reservoir (for example a syringe) having a longitudinal axis perpendicular (and/or at a large angle for example between 90 to 80 degrees and/or 80 to 60 degrees and/or between 60 degrees to 30 degrees) to a skin contact surface or a base. Optionally, the long axis of the skin contact surface and/or base of a stabilized pen injector may be shorter than the height of the injector perpendicular to the skin contact surface.

In some embodiments, needle insertion and/or retraction and/or protection may be automatic. For example, movement of a needle and/or a needle shield (e.g. insertion and/or retraction and/or deployment of a shield and/or withdrawal of the shield) may be powered by an actuator (for example a piston and/or a magnet) and/or a stored energy source (for example a spring and/or a battery). Alternatively or additionally, movement of a needle and/or a needle shield (e.g. insertion and/or retraction and/or deployment of a shield and/or withdrawal of the shield) may be manually powered, for example by pushing an injector and/or a button towards an injection site and/or by pulling the injector away from the site.

DETAILED EMBODIMENTS

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Flow Chart of an Exemplary Method of Needle Protection

FIG. 1A is a flow chart illustration of a method of protecting a needle in accordance with an embodiment of the present invention. In some embodiments, a needle is protected automatically when the device is moved away from an injection site.

Optionally the needle is protected before a skin contact surface of the device is removed from the site. For example, the needle may be protected from temporary exposure while the device is being removed. For example, the device may include a base attached to the subject and a body. A needle retraction mechanism may include interlocked parts connected to body and the base. Pulling the body away from the subject may extend the body away from the base and/or disengage the interlocked parts of the retraction mechanism. For example, disengaging the interlocked parts may unlock the needle and/or trigger retraction of the needle.

In some embodiments, an injection device may have an active state 112 wherein a skin contact surface of the device is connected to a needle insertion site, for example on the skin a subject. In the active state 112, a needle is optionally extended into the subject. Optionally, a locking mechanism maintains the needle in the extended position. Alternatively or additionally, the device may include a needle protection mechanism. The locking mechanism and/or needle protection mechanism optionally includes at least one part that moves with the base interlocked to at least one part that moves with the body.

In some embodiments, a user will move 114 the body of the device, for example in order to remove the device from an injection site. Optionally, the user may start removing the device by an intuitive movement. For example, removal may be by pulling the body away from the skin. Optionally, while the body is moved by the user, the skin contact surface remains attached 115 Moving 114 the body optionally causes relative movement 116 between the base and the body.

In some embodiments, the user is encouraged to pull the body from a specific location on the body and/or in a specific direction. For example the housing may have some surfaces that are difficult to pull (for example then are convex and/or face away from the surface and/or low friction) and/or other surfaces that are configured to easily be pulled (for example including indentations for gripping and/or a high friction coating and/or angled toward the skin contact surface). Optionally, there may be markings instructing the user to pull here and/or remove from here etc.

In some embodiments, the body and base of the injector may be free to move relative to each other and/or biased to move relative to each other. Alternatively or additionally, relative movement between the body of the injector and the skin contact surface may be inhibited by a retaining mechanism. For example, the body may be attached to the same surface as the base and/or the body and base may be biased toward one another. Optionally, the when causing relative movement between the base and the body of the injector, the user may overcome the retaining mechanism. For example, the user may detach the body from the injection site while the base remains attached to the injection site. Alternatively or additionally, at certain times, relative movement may be inhibited (for example during drug delivery) and at other times, relative movement may be facilitated.

For example, at the end of injection the retaining mechanism may be automatically nullified. For example, nullifying the retaining mechanism may facilitate relative movement. Alternatively or additionally, the body of the injector may move on its own respective to the base (e.g. pop up away from the injections site). Optionally, when the retaining mechanism is nullified, the device may remain attached (e.g. by the base) to the injections site.

In some embodiments, relative movement 116 between the base and the body may further cause relative movement between 117 interlocked parts in the needle protection mechanism. The relative movement 117 of parts of the protection mechanism may initiate 118 protection of the needle tip. For example, relative movement 117 may unlock a needle (e.g. allowing it to retract) and/or unlock of a needle shield (e.g. allowing it to extend to cover the needle). For example, relative movement 117 may trigger movement of a needle (e.g. triggering retraction of the needle point) and/or trigger movement of a needle shield (e.g. extending it to cover the needle). For example, initiating 118 and/or initiating protection may include by retracting the needle and/or shielding the needle.

In some embodiments, the device may be removed 120 from the user after the needle is protected. For example, the skin contact surface may be pulled and/or peeled from the injection zone.

Flow Chart of an Exemplary Method of Initiating a Drug Delivery Device

Figure 1B:
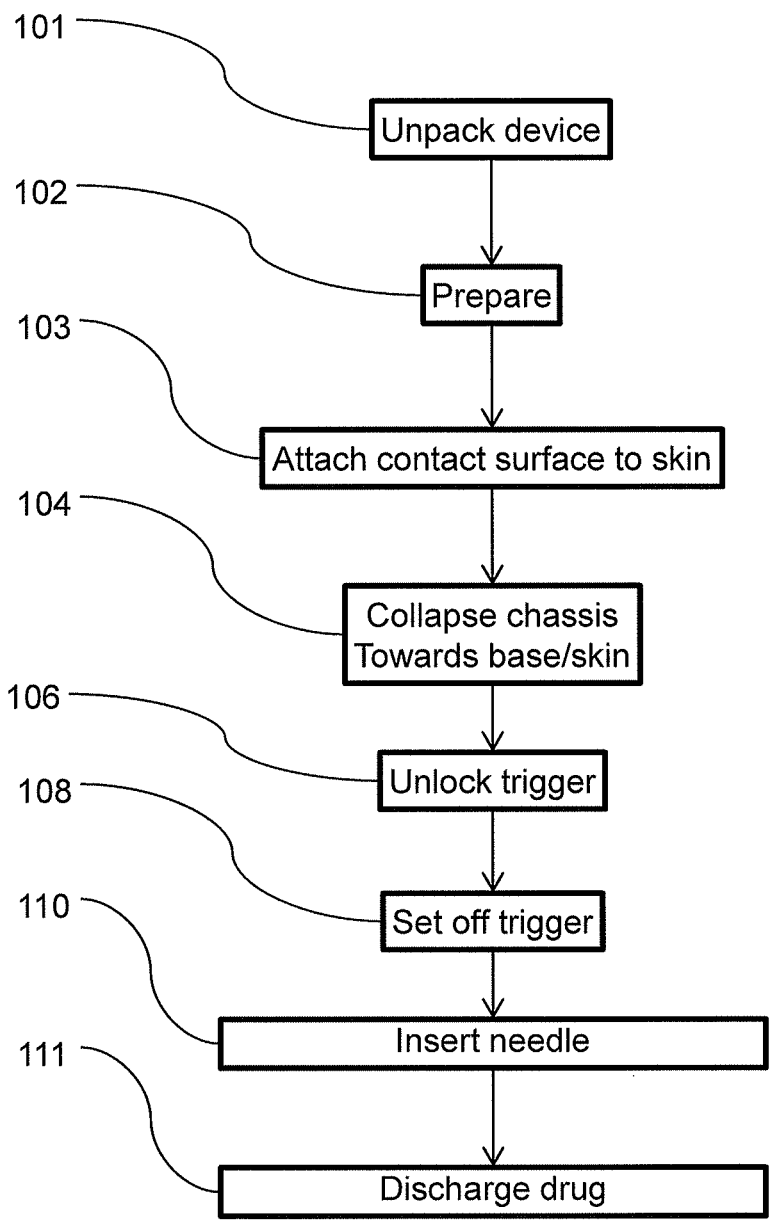
FIG. 1B is a flow chart illustration of a method of extending a needle in accordance with an embodiment of the present invention.

FIG. 1B is a flow chart illustration of initiation of a drug delivery device.

Optionally initiated the device may include extending a needle in accordance with an embodiment of the present invention. Optionally, a user prepares a patch injector for use by simple intuitive steps. Optionally, multiple steps may be performed simultaneously with one act and/or sequentially and/or with multiple acts. Optionally, the a step in preparing the device will cue the user toward the next step, which may include a logical continuation of the preparing. The initiation of the device may be intuitive and/or robust against failure even when misused and/or avoid exposing of a user to hazards under various conditions (proper use, misuse and/or failure).

In some embodiments, the device may be packaged in a way that presents the device in a proper orientation for further preparation of the device. For example, when the packaging is open, the device may be presented to the user in a way that encourages gripping of the device in the proper way for further initiation steps. For example, a griping surface and/or a surface opposite the skin contact surface of the device may be presented to the user upon opening the packaging.

In some embodiments, the packaging may expose a user interface in an early part of unpacking the device. For example, the user interface may be viewable through a window in the packaging before the package is fully opened. Alternatively or additionally, the packaging may be designed such that when the package is opened the user interface faces the user.

Alternatively or additionally, the device may be placed in the packaging such that when the device is unpacked 101 (for example, when it is removed from the packaging) the user interface is exposed to the user. Optionally, the user interface may include familiar operational features. For example, features may include a manually operated feature (for example a pull tab, a pull ring, and/or a button) and/or a display (for example a screen and/or a light and/or a window). The position of the feature may encourage the user to hold the device with the feature operable and/or with the display visible (for example directing his gripping of the device not to cover up a feature and/or orienting the device such that the feature faces the user's limbs and/or eyes).

In some embodiments, a user may prepare 102 a device for use. For example, preparing a device for use may include removing a sterile needle cap and/or removing a protective liner from a skin contact surface. Optionally, multiple components of the device may be interconnected and/or prepared together. For example, a protective needle cap and an adhesive liner may be connected to a single handle, for example a pull ring. Pulling the pull ring optionally removes the cap and the liner together.

Alternatively or additionally, preparing 102 one part may start a process that enables and/or causes preparing 102 of another part.

In some embodiments, a drug delivery device may be attached to a subject. For example, the device may include a skin contact surface that is attached 103 to the skin of the subject. Optionally, attachment 103 is by means of an adhesive. Optionally, the device and/or packaging thereof may be designed to encourage the user to properly attach the device. For example, the skin contact surface may be larger and/or flatter than another surface of the device that does not contact the skin. In some embodiments, the presence of adhesive on the contact surface of the device will serve as an intuitive clue to the user that this surface should be attached to the skin. Optionally, a surface of the device that is not to be attached to the subject may include a feature that intuitively should be exposed, for example an operation feature of the device (e.g. a display and/or a control interface).

In some embodiments, a drug delivery device may include a safety feature to prevent drug delivery before certain steps are performed. For example, in some embodiments, a skin contact surface may serve as a skin sensor. The device may be designed to inhibit extension of a needle and/or discharge of a drug unless the skin contact surface is in contact and/or attached to the subject. For example, an activation button of a drug delivery device may be locked until a skin sensor registers placement of the device on an injection site. For example, the skin sensor may include a skin contact surface. Optionally, when the device has been prepared for use, an activation button may be locked. The button is optionally unlocked 106 by collapsing 104 the skin contact surface into device (for example placing the contact surface onto the injection site and pushing the body of the device towards the skin).

In some embodiments, a drug delivery device may insert a needle through the skin of a subject and/or discharge a drug to the subject. For example, once an activation button is unlocked, pushing the button may cause needle insertion 110 and/or drug delivery 111. In some embodiments, needle insertion is automatic, for example, pressing an activation button may trigger 108 a spring based needle insertion. Alternatively or additionally, force of the user pushing on the activation button may manually extend the needle into the injection site. Alternatively or additionally, the needle may be inserted when the sensor senses contact with the injection site. For example, the user may push the device onto the injection site, collapsing a base of the injector inward, exposing the needle. Alternatively or addition, a sensor may trigger a needle extension mechanism when it senses contact with the injection site.

State Diagram of an Injector

Figure 2A:
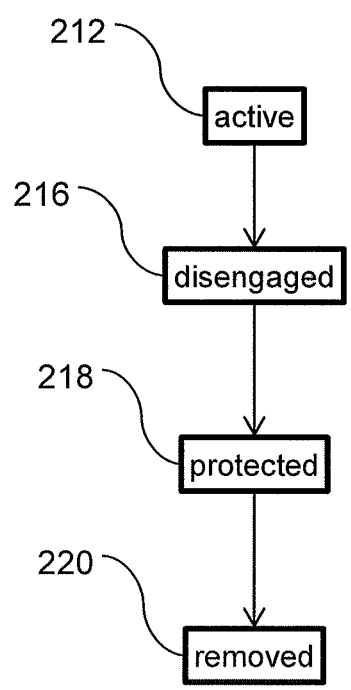
FIGS. 2A and 2B are a state diagram illustration of an injector in accordance with an embodiment of the present invention.

FIG. 2A is a state diagram illustration of detaching an injector in accordance with an embodiment of the present invention. In some embodiments, an injector may have an ordered set of detachment steps. Optionally some or all of the steps are irreversible. For example, in an active state 212 an attachment surface of the device may be attached to an injection site and/or engaged to body of the device. Disengaging the attachment surface of the device from the body of the device optionally switches the device to a disengaging state 216. Switching the device to disengaging state 216 optionally causes the device to switch to a protected state 218. The device is optionally removed 220 from the injection site after switching to the protected state.

In some embodiments, an injection device may have an active state 212. For example active state 212 may include a working state (e.g. while the device is delivering a drug to a user) and/or a waiting state (e.g. while the device is waiting before delivering a drug and between multiple drug deliveries events and/or after completing delivery).

Optionally, in active state 212 an attachment surface of the device is attached to an injection site and/or supports the device on an injection site. Optionally, in active state 212, a delivery channel, for example a needle and/or a cannula, protrudes into the user at the injection site. For example, the delivery channel may protrude into the user through an opening in the skin contact surface.

In some embodiments, in active state 212, the base of the device may be engaged to the body of the device (for example the body of the device may include a housing of the device and/or a needle driver). For example, the base may be interlocked to the needle driver to lock the needle in an extended position. For example, a part that is attached to the base and/or moves with base may interlock to a part that is attached to the body of the device and/or moves with the body of the device. Alternatively or additionally, in the working state 212 the base may be retained engaged to the body. For example, engagement between the body and the base may expose a needle tip (for example the base may collapse against the body of the device to expose the needle protruding through an opening in the base). Optionally, the base and body may be retained in the engaged state by mutual connection to an external object (for example a surface, for example an area around an injection site). Alternatively or additionally, the base and body may be retained together by a locking mechanism.

In some embodiments, before removing a delivery device from a user, the device may be switched to a disengaged state 216. For example, switching the device a disengaged state may include disengaging the base from the body of the injector.

Optionally the body is disengaged from the base while the base remains attached to the injection site.

In some embodiments, a user action may switch the device from the active to the disengaged state. For example, the user may the pull the body of the device away from the base of the device to disengage the base from the body. Optionally, the user may overcome a retaining mechanism to disengage the base from the body of the device. Alternatively or additionally, under certain conditions, the base may automatically be disengaged from the body of the device. For example, upon completion of drug delivery the body of the device may automatically be disengaged from the base.

In some embodiments, the disengagement is partial. For example, the base may be disengaged from the body by distancing the body from the base while the base still supports the body and/or connects the body to the injections site.

In some embodiments, disengaging a base of the device from a body of the device may trigger and/or facilitate protection of a delivery channel. For example, in the active state a needle may be locked with a needle point in an extended position. The locking mechanism may include engaged parts connected to the body and/or base of the device. Disengaging the base from the body optionally rearranges the engaged parts and/or unlocks the needle allowing the needle to be retracted and/or facilitating retraction of the needle.

In some embodiments, disengaging the base from the body of the device causes the device to switch to a protected state 218. For example, a movement between the base and the body of the device may cause retraction of a needle tip through an opening of the base of the device into a protected position. Alternatively or additionally, relative movement between the base and the body of the device may cause extension of the base to a position shielding the needle. In the protected state 218, the base optionally remains attached to the injection site. Alternatively or additionally, in protected state 218 the base may support the body on the injection site.

In some embodiments, in protected state 218, the device may be removed 220 from the injections site. Optionally, in protected state 218 the needle may be retracted making it easier to separate the device from the injection site. For example, the base may be peeled from the injection site without moving the needle inside the skin of the user and/or without exposing the user to a sharp stick hazard.

Figure 2B:
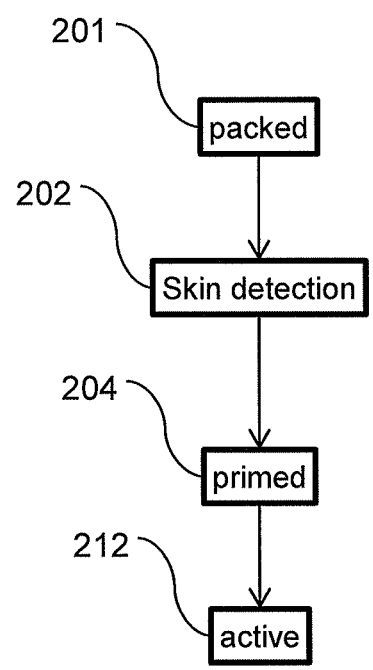

FIG. 2B is a state diagram illustration states of attaching an injector in accordance with an embodiment of the present invention. Optionally, the device is delivered to the user in a packed state 201. Optionally the user unpacks the device and/or prepares the device for attachment to an injection site. For example, a skin sensor may be deployed to put the device in a skin detection state 202. The device may be attached to an injection and/or pushed toward the injection site. Pushing the body of the device towards the injection site optionally stimulates the skin sensor (for example by collapsing a base of the device towards a body of the device). Stimulating the skin sensor optionally switches the device into a primed state 204. Optionally a user action may activate the device from primed state to active state 212. For example, stimulating the skin sensor may enable an activation button and/or pushing the activation button may active the device into active state 212.

Patch Injector

Figure 3:
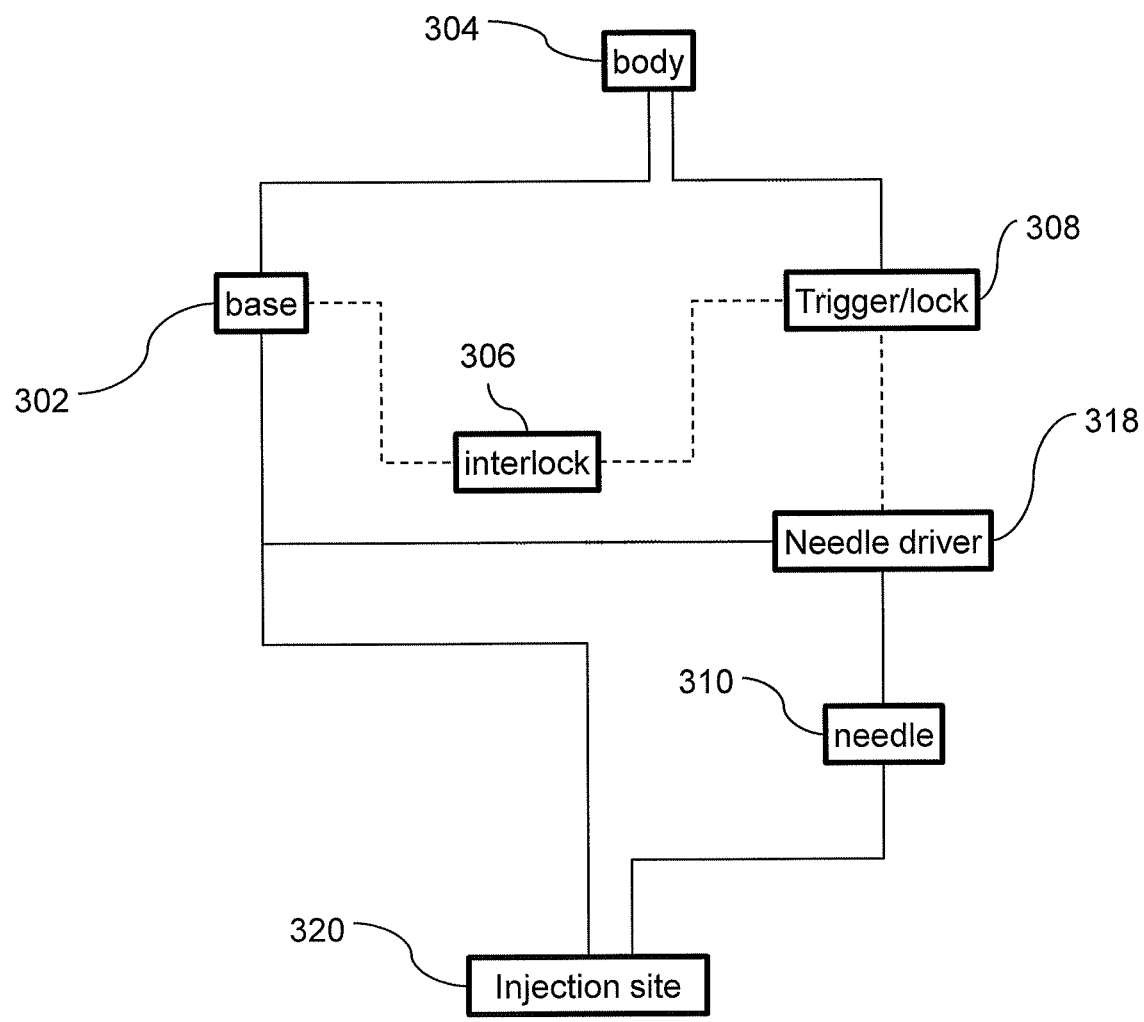
FIG. 3 is a block diagram illustration of a of needle insertion and/or retraction mechanism in accordance with an embodiment of the present invention.

FIG. 3 is a block diagram illustration of an insertion and/or a retraction mechanism in accordance with an embodiment of the present invention. In some embodiments, a base is attached to an injection site. Optionally, the base supports a body of the injector and/or a needle driver. For example, the body may be movably connected to the base. The driver is optionally controlled by a trigger and/or a locking/triggering mechanism. Optionally, the trigger and/or locking mechanism is actuated by the position of the base relative to the body. For example, a mechanical trigger may be mechanically interlocked between the body and base.

In some embodiments, base 302 may include a contact surface configured to attach to an injection site 320. For example, the contact surface may include an adhesive configured to adhere to skin of injection site 320. Optionally, the adhesive on the base is strong enough to support the weight of the entire device. For example, the adhesive may hold the device from falling when the weight is pulling the device away from the injection site and/or the adhesive may prevent sheering movement of the device when the weight is directed parallel to the injection surface. For example, the adhesive on the base may have a surface area between 1 $cm^2$ to 5 $cm^2$ and/or between 5 $cm^2$ to 15 $cm^2$ and/or between 15 $cm^2$ to 80 $cm^2$ or more. Optionally, the adhesive on the base will have a flexible skirt. For example, the skirt may have a length of between 1 mm to 5 mm or between 5 mm to 20 mm or more.

In some embodiments, a body 304 of the device may be connected to the base. For example, the body of the device may include a housing and/or a chassis and/or an energy source and/or a drug reservoir and/or an actuator and/or a pump for discharging the drug through a delivery channel and/or through the injection site into a subject.

Optionally, body 304 and base 302 are connected for relative movement. For example, while base 302 remains attached to injection site 320, body 304 may move relative to the injection site. Optionally, body 304 and base 302 may be connected via a hinge and/or a sliding joint.

In some embodiments, a needle driver 318 may drive insertion and/or retraction of a deliver channel, for example including a needle 310. For example, needle driver 318 may include an elastic element driving movement of needle 310 with respect to the contact surface of base 302. For example, driver 318 may drive extension a sharp tip of needle 310 through an opening in base 302 into the injection site and/or driver 318 may retract the tip of needle 310 through the opening in base 302 back from the injection site. Optionally, driver 318 is mounted to base 302. Alternatively or additionally, driver 318 may be mounted to body 304.

In some embodiments, needle driver 310 is controlled by a locking/triggering mechanism 308. For example, mechanism 308 may trigger retraction and/or extension of needle 310. Optionally mechanism 308 may respond to changes in the relative positions of body 304 and base 302 to trigger retraction and/or extension. For example, when needle 310 is extended, mechanism 308 may retract needle 310 in response to a movement of body 304 away from base 302. For example, when needle 310 is locked in an extended position, mechanism 308 may unlock needle 310 in response to a movement of body 304 away from base 302. In some embodiments, a mechanical linkage may interconnect 306 mechanism 308, base 302 and/or body 304. For example, relative movements of the components may cause physical locking/unlocking and/or trigger insertion/retraction. Alternatively or additionally, mechanism 308 may include an electronic sensor, an electrical switch and/or a logic processor and/or an optical sensor sensitive to relative movements of base 302 and body 304.

In some embodiments, the system may be biased towards retraction and/or extension of needle 310. For example, base 302 may be biased toward body 304 and/or away from the body. Optionally a retaining mechanism may hold body 304 and/or base 302 in a fixed configuration. Optionally a user action will overcome biasing and/or a retention mechanism to extend and/or retract and/or lock and/or unlock needle 310.

For example, in some embodiments, base 302 may be biased away from body 304. Optionally, in an active state, base 302 and body 304 are both attached to an injection site. When a user pulls body 304 away from the injection site, base 302 stays on the site and/or is distanced from base 302. Optionally, distancing base 302 from body 304 triggers needle retraction.

In some embodiments, a discharge mechanism and/or a user interface and/or a logical controller are sensitive to the relative positions of base 302 and body 304. For example, an activation button for discharge may be blocked when base 302 is distanced from body 304. Alternatively or additionally, a logic unit may register and/or communicate an error condition when base 302 moves with respect to body 304 in a way that is not according to the specified order of operation of the device. Optionally the error may lead to locking and/or stopping and/or disabling of certain systems of the device. For example, premature distancing of base 302 from body 304 during drug discharge may cause an error condition and/or cause a stopping of drug delivery. For example, the base may move with respect to the body between 0.1 mm to 1.0 mm and/or between 1 mm to 2 mm and/or between 2 mm to 4 mm and/or between 4 mm to 10 mm and/or between 10 mm to 30 mm. For example, the distance moved may be measured where the maximum relative movement occurs.

Figure 4A:
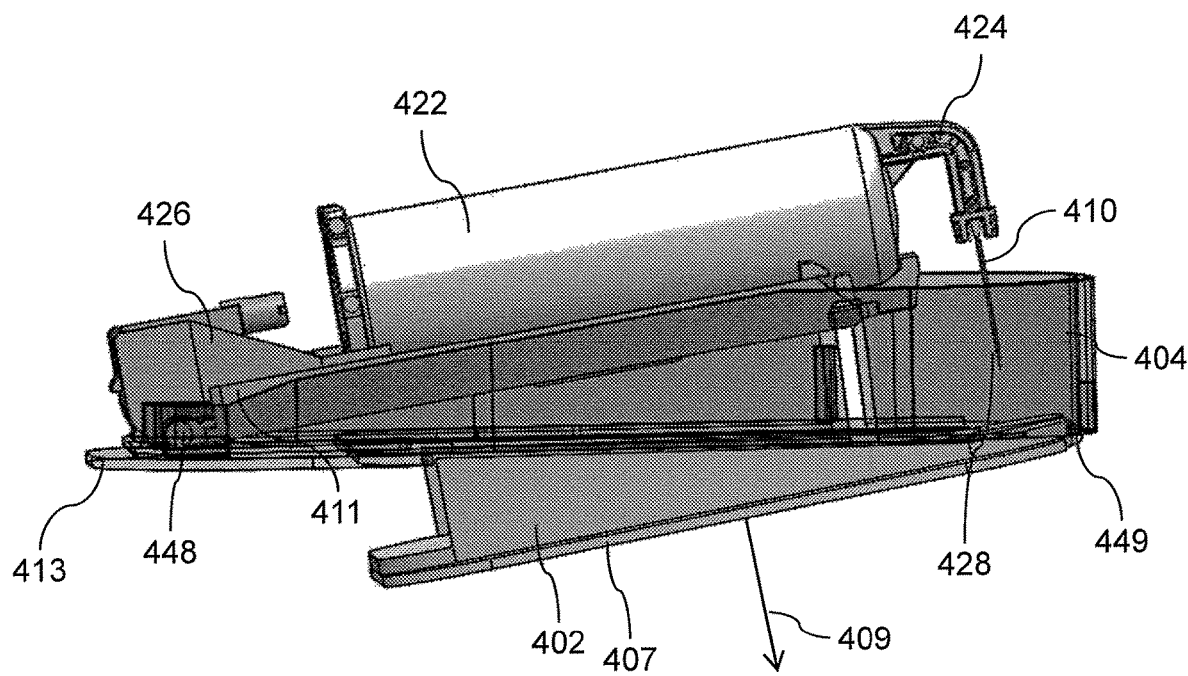
FIGS. 4A-4D are side view illustrations of a four states of an injector in accordance with an embodiment of the present invention.
Figure 4B:
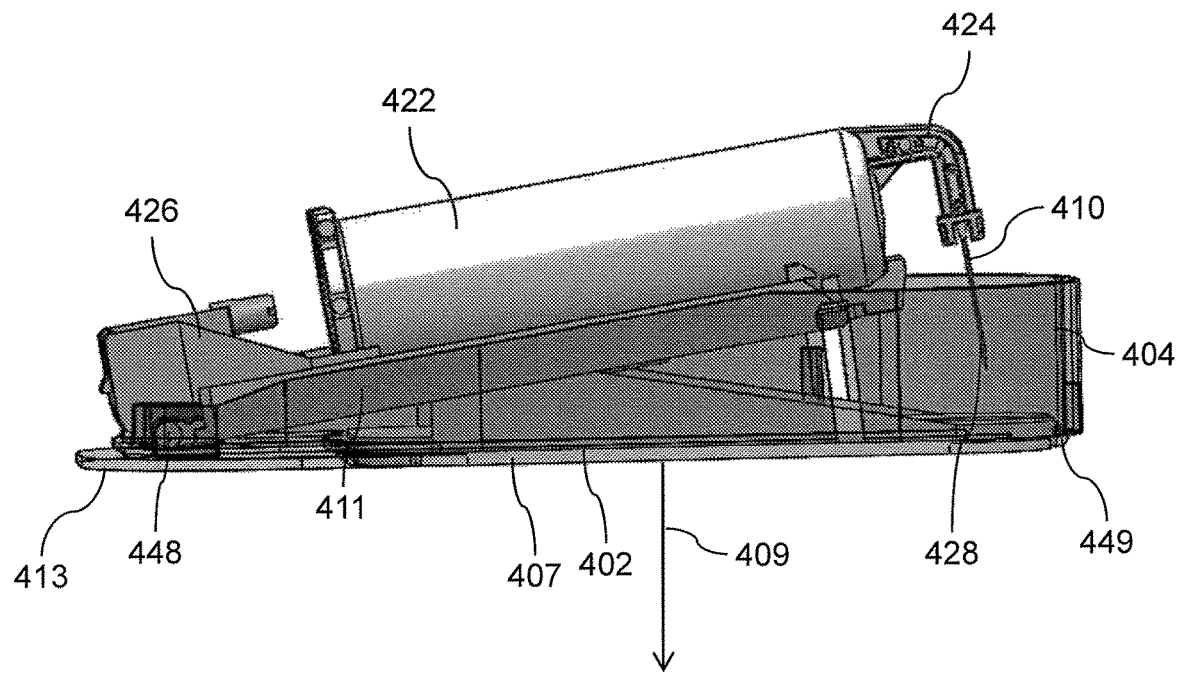
Figure 4C:
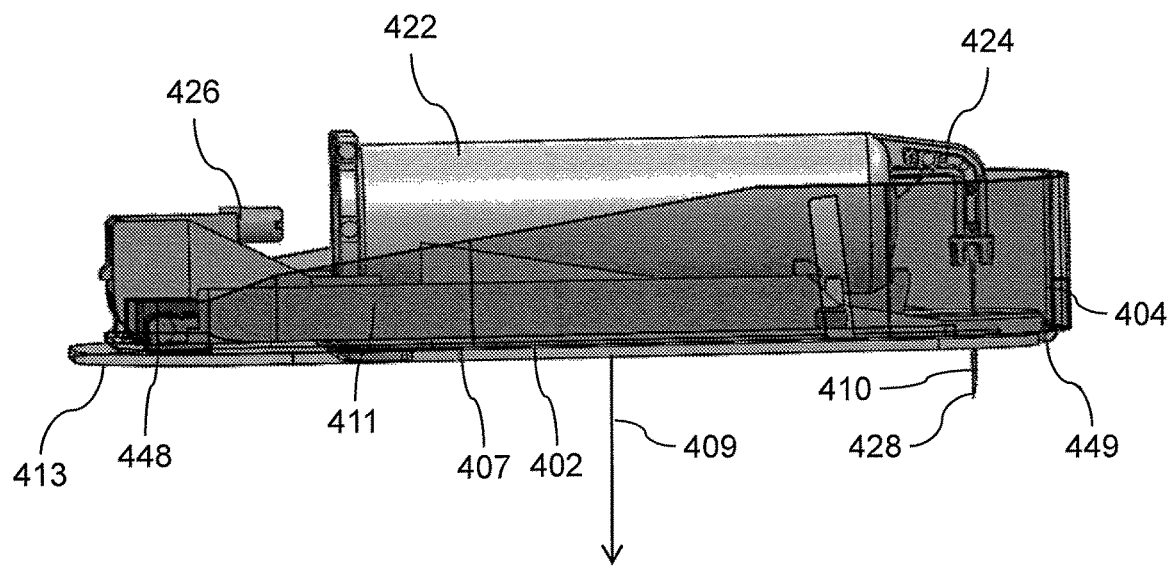
Figure 4D:
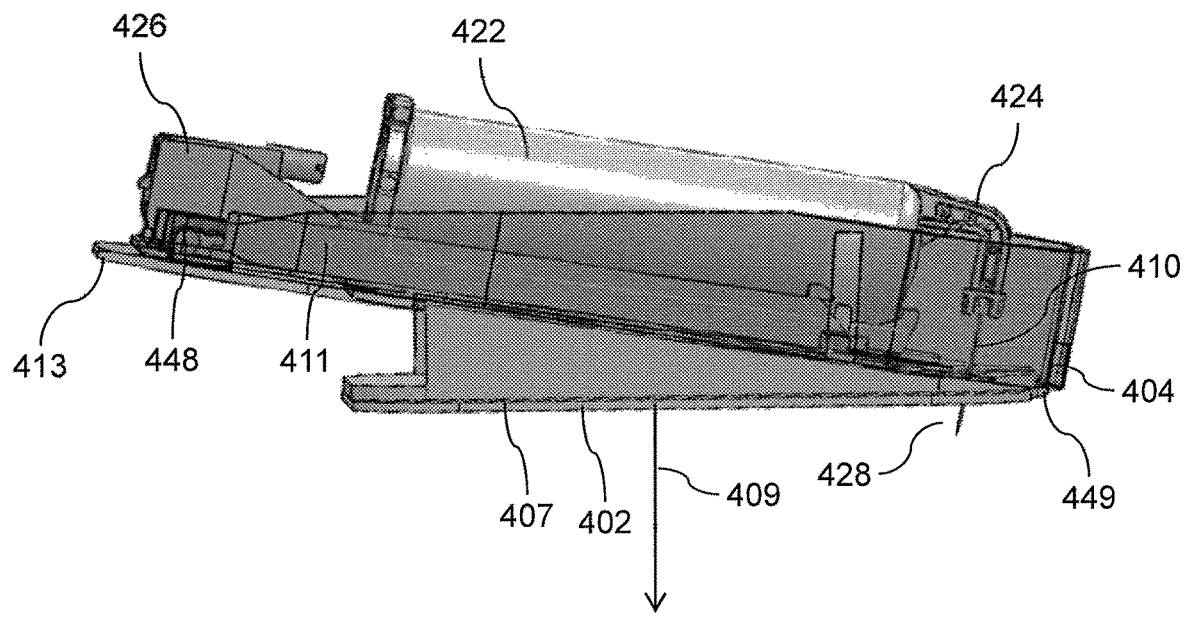

FIGS. 4A-4D are side view illustrations of a four states of an injector in accordance with an embodiment of the present invention. For example, FIG. 4A illustrates the injector in an optional skin detection state. For example, FIG. 4B, illustrates the device in an optional unlocked and/or primed state. For example, FIG. 4C, illustrates the device in an optional active state. For example, FIG. 4D illustrates the device in an optional unlocked removal state. Optionally, needle retraction may return the device from the unlocked removal state to a protected state, for example with the needle positioned as illustrated in FIG. 4A.

In some embodiments, an injector may be supplied with in a locked state. For example, the user may prepare the device by unpacking it, opening the device (for example releasing a base of the device to an extended state). For example, preparing the device may include removing a protective cap and/or removing a protective covering. For example, an adhesive protector may be removed from a skin contact surface on the base of the injector and/or on the body of the injector. Optionally, during unpacking and/or preparing the device, the device may be connected to a power source and/or a computing device (for example a personal computing device of the user). For example, a set of live instructions may be displayed. Optionally preparing the device places the device into a skin detection state. For example, removing the needle cap and/or adhesive protector may extend a base and/or a skin sensor. For example, removing the needle cap and/or adhesive protector may unlock the base and/or the skin sensor for example allowing them to collapse toward the body of the device when attached to an injection site.

FIG. 4A illustrates an injector in an optional skin detection state in accordance with an embodiment of the present invention. For example, in the skin detection state a needle tip may be locked and/or protected inside a body. For example, a needle tip 428 may be surrounded on three sides by a chassis 404 of the body. Optionally, in the skin detection state the needle is locked in the protective state until the injector interacts with and/or is connected to an injection site. For example, the needle may remain in the locked position until at the base of the injector is attached to an injection site and/or the body of the injector is pushed towards the base.

In some embodiments, in the skin detection state, base 402 of the device may be extended away from body of the device. For example, a rear portion of base 402 is pivoted away from chassis 404. Optionally, base 404 includes a skin contact surface 407 on a bottom surface thereof. A vector normal 409 to skin contact surface 407 optionally points away from the body of the device. For example, traveling from surface 407 in the direction of normal 409 may move away from a center of gravity of the body.

Alternatively or additionally traveling from surface 407 in the direction of normal 409 may move away from a nearest point on the body.

In some embodiments, base 402 of the injector may be attached to the skin of a subject (for example at an injection zone) while the device is in the skin detection state.

Optionally after attachment, the chassis 404 is moved towards the base and/or the skin to facilitate activation of the device. For example, facilitating activation of the device may include triggering needle insertion. Alternatively or additionally, facilitating activation of the device may include unlocking an activation switch and/or a needle insertion trigger. Alternatively and/or additionally, attaching the base 402 and moving chassis 404 towards the injection site may be a continuous process. For example, as the user pushes the prepared device onto the skin, first, the contact surface of the base 402 of the device contacts the skin and/or then the chassis 404 is pushed toward the base and/or the skin.

In some embodiments, in the skin detection state, prior to activation, the skin contact surface of the injector may be biased away (for example outward) from the body of the injector. For example, base 402 is biased away from chassis 404. Base 404 is optionally collapsed towards chassis 404 by overcoming the outward biasing force.

Optionally, a retaining force is supplied to retain base 402 in the collapsed state. For example, chassis 404 may include a contact surface 413 and/or an adhesive that retains base 402 in the collapsed state. Optionally, after base 402 is attached to the injection site and/or base 402 collapses into chassis 404, surface 413 contacts and/or attaches to the skin. Attachment of surface 413 to the skin optionally holds base 402 collapsed together with chassis 404. Alternatively or additionally, base 402 may be biased toward chassis 404. Alternatively or additionally, biasing and/or a retaining force may change based on a state of the injector. For example, when drug delivery is completed In some embodiments, the attachment mechanism of the injector may be interlocked to a needle driver and/or a needle extension mechanism. For example, needle 410 is rigidly mounted to an extension 424 of a cartridge. Cartridge 422 is optionally rigidly mounted to a plate 411, which is connected to and/or moves with respect to chassis 404. For example, plate 411 is configured to rotate around a pivot

448. For example, pivot 448 may be fixed in relation to chassis 404 and/or mounting plate 411 may rotate around a location on chassis 404. Movement of plate 411 around pivot 448 optionally causes needle 410 to move longitudinally (for example in an arc trajectory) from a protected position (for example inside the body as illustrated in FIG. 4A) to an extended position (for example with point 428 projecting outward from the body and/or surface 407. Optionally, when base 402 and/or attachment surface 407 are extended away from the body, plate 411 may be locked in a retracted position and/or needle point 428 may be locked in the protected position.

In some embodiments, in the skin detection state, a needle 410 of the injector is substantially perpendicular to contact surface 407 of base 402 (for example needle may range between 0 to 2 degrees and/or 2 to 5 degrees and/or 5 to 10 degrees and/or 10 to 20 degrees and/or 20 to 45 degrees from parallel to normal 409). For example, the orientation of needle 410 to surface 407 may facilitate preparation of the device for example including removal of a needle cap and/or adhesive protector.

Some embodiments may include a plunger driver. For example, a plunger driver may include a telescoping screw assembly 426 and/or a motor and/or a battery and/or a transmission. Alternatively or additionally, a plunger driver may include an expanding gas and/or linear actuator and/or a piston.

FIG. 4B, illustrates the device in an optional unlocked and/or primed state in accordance with an embodiment of the current invention. For example, after attaching the base of the injector to an injection zone of the skin of a subject, the base may be collapsed toward the housing and/or chassis of the injector. For example, a user may collapse the base of the injector towards the body by pushing the body towards the base and/or the skin of the subject.

Optionally, base 402 is interconnected to a lock that keeps needle 410 in the retracted position. For example, collapsing base 402 toward the body may unlock the needle 410 and/or a needle driver. For example, plate 411 may rotate around a pivot 448 to extend needle 410. For example, collapsing base 402 may unlock an activation switch of the injector. Activating the injector optionally triggers a needle driver, to drive needle point 428 into the extended position and/or into the skin of a subject.

FIG. 4C, illustrates the injector in an optional active state. In the active state, a sharp needle tip optionally extends out from the body and/or through the base of the injector. For example, the needle tip may project past skin contact surface 407 into the skin of a subject. In the active state, medicinal substance, for example a drug, is optionally injected through needle 410 into the subject.

In some embodiments, needle tip 428 is inserted into a subject by a rotating needle driver. For example, the needle drive drives plate 411 to rotate around joint 448.

Optionally, in the active state, a longitudinal axis of a barrel of cartridge 422 is substantially parallel to skin contact surface 407 and/or base 402. For example, hinge 448 and hinge 449 are at opposite sides of the injector and/or rotate in the same direction. Alternatively or additionally, two hinges may be on the same side of the device and rotate in opposite directions. Rotation of one hinge may compensate for movement of another hinge such that the relationship between the injector cartridge and the base during the active stage is similar to the relation between the cartridge and the base in the skin detection state (for example before placing the device onto the skin of the user).

For example, in the skin detection state and/or in the active state the base 402 may be parallel to the longitudinal axis of the cartridge 422. For example, in the skin detection state and/or in the active state the base 402 may be perpendicular to the longitudinal axis of needle 410. In some embodiments, in the active state, a needle 410 of the injector is substantially perpendicular to contact surface 407 of base 402 (for example needle may range between 0 to 2 degrees and/or 2 to 5 degrees and/or 5 to 10 degrees and/or 10 to 20 degrees and/or 20 to 45 degrees from parallel to normal 409). For example, the orientation of needle 410 to surface 407 in the active state may be the same or similar to the orientation of needle 410 to surface 407 in the skin detection state. For example the difference in the angle between 410 to surface 407 in the active state to the skin detection state may be range between 0 to 3 degrees and/or between 3 to 10 degrees and/or between 10 to 30 degrees.

In some embodiments, base 402 may remain in a collapsed state until the user pulls the body away from the skin. Optionally, an additional skin contact surface may be brought into contact with the skin of the user when the base collapses. For example, an additional contact surface 413 may be on the body of the injector. For example, surface 413 may have an adhesive. Optionally, adhesion of surface 413 to the skin of the subject may inhibit movement of the body away from the skin and/or keep base 402 in the collapsed state. Alternatively or additionally, there may be a locking mechanism that holds base 402 collapsed during the primed and/or active states of the device.

Alternatively or additionally, the bias of base 402 with respect to the body may depend on the position of base 402 with respect to the body and/or may be depend on the state of the injector.

In some embodiments, a lock may not be released until a threshold force is applied to the body of the device and/or until a section of the body of the device (for example contact surface 413) moves in relation to base 402. For example, contact surface 413 may be biased outward, inward and/or backward and/or interconnected with a lock so that base 402 is released when surface 413 is moved with relation to base 402 and/or the injection zone. Optionally a lock may be released at the end of discharge of a drug and/or upon malfunction of the injector making it easier to trigger needle release. Optionally, releasing the lock may require a pulling the body away from the skin with a particular direction, force, and/or over a minimal time period. For example, unlocking base 402 only for a particular combination of force and/or direction and/or time may avoid base 402 being released unintentionally (for example do to momentum caused by movements of the subject.

FIG. 4D illustrates the device in an optional unlocked removal state. For example, pulling the body of the injector away from base 402 and/or an injection zone of a subject may extend skin surface 407 and/or base 402 away from a body of the injector. Optionally, when the body of the device is distanced away from skin contact surface 407, a needle driver may be triggered to retract needle 410 into a protected location. Optionally triggering retraction may include unlocking a needle release mechanism of the needle driver and/or initiating a needle release mechanism of the needle driver. For example retracting the needle may return device to the configuration of FIG. 4A. Optionally, when needle 410 is retracted, it may be locked. Locking needle 410 in the retracted configuration may place the device into a protected state.

Optionally, after needle retraction, needle 410 may be inhibited from being reexposed. For example, the needle exposure process described above with respect to FIGS. 4A, 4B and/or 4C may be blocked when needle 410 is retracted.

Optionally, base 402 is biased away from the body. Biasing optionally extends base 402 away from the body whenever there is no force preventing extension. For example, base 402 may extend away from the body when surface 413 is separated from the skin regardless of whether the body is pulled away from base 402 or the separation is due to other factors (for example peeling the adhesive from the skin). Alternatively or additionally, base 402 may be biased toward the body. For example, extension of base 402 may be due to adhesive forces pulling contact surface 407 towards the injection site as the body is pulled away from the injection site.

Figure 5A:
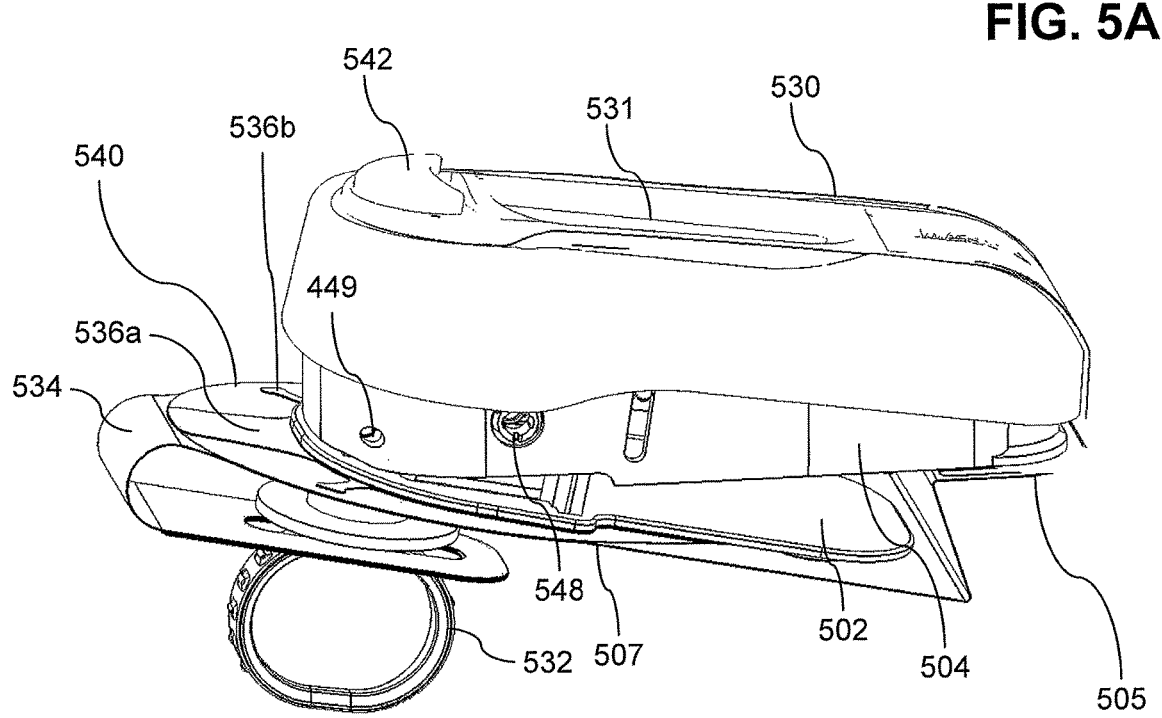
FIGS. 5A and 5B are a perspective view illustrations of an injector in accordance with an embodiment of the present invention.
Figure 5B:
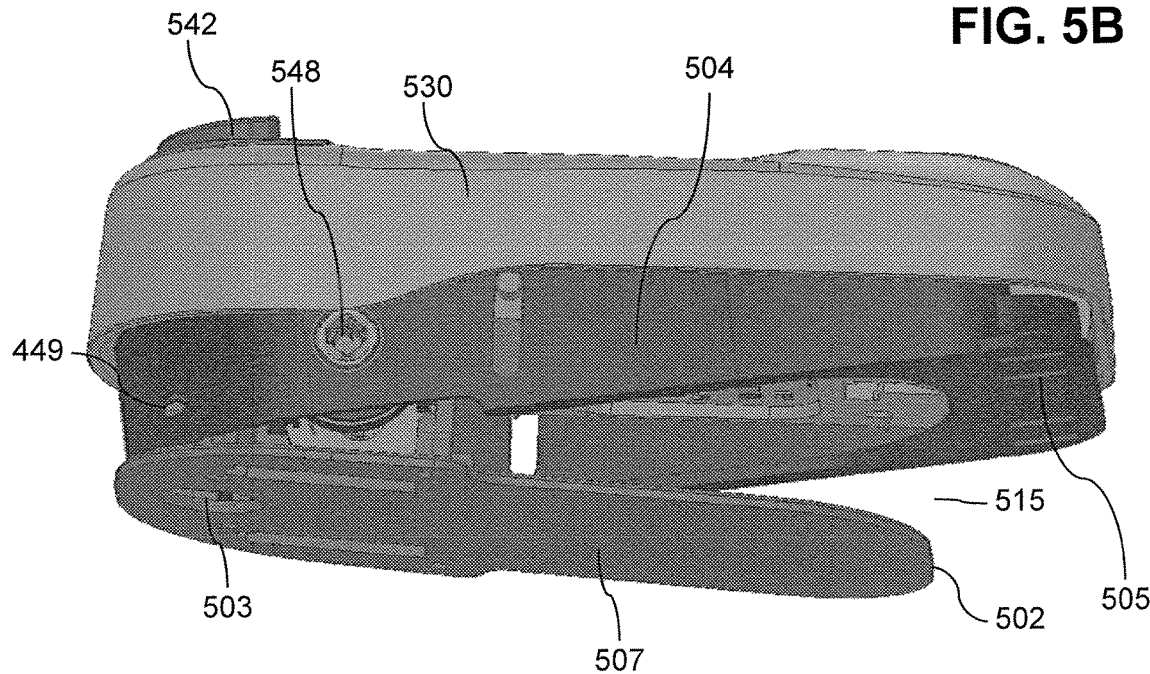

FIGS. 5A and 5B are a perspective view illustrations of an injector in accordance with an embodiment of the present invention. In some embodiments, an injector includes an extendable base. The extendable base may be interconnected to a needle driver such that collapse and/or extension of the base facilitates and/or triggers needle insertion and/or retraction.

Optionally the base includes a skin contact surface. For example, the skin contact surface may include an adhesive. For example, the adhesive may be configured to adhere the contact surface to the skin of a subject, for example near and/or surrounding a needle insertion site. The injector is optionally configured to encourage intuitive placement and/or removal of the device and/or intuitive triggering of needle insertion and/or retraction.

FIG. 5A illustrates an injector with an adhesive and needle cover in accordance with an embodiment of the current invention. In some embodiments, an injector includes a body and a base 502 movably mounted to the body. For example, a body may include a housing 530 and a chassis 504. Base 502 is optionally movably attached to chassis 504. For example, base 502 moves rotationally around a pivot 449 connected to chassis 504.

In some embodiments, features on the injector encourage intuitive understanding of placement of the injector on the skin. For example, one or more skin contact surfaces 507, 505 of the injector may include an adhesive 540. Adhesive 540 may be covered with an adhesive protector liner 534. Preparing the injector for use optionally includes peeling one or more adhesive liners 534 off of adhesive 540. Peeling adhesive liners 534 from adhesive 540 clues the user to the need to place and/or stick surfaces 507 and 505 to the skin. Optionally, in the skin detecting state contact surfaces 505 and 507 may not form a continuous surface. For example, there may be a gap. For example, the gap may range between 0.1 and 0.3 cm and/or between 0.3 and 0.6 cm and/or between 0.6 to 1.2 cm and/or between 1.2 to 2.4 cm and/or greater than 2.4 cm.

A user may intuitively understand that he should place the protruding contact surface 507 against the skin and then push against the body to collapse gap 515 and bring contact surface 505 into contact with the skin. In some embodiments a single adhesive liner 534 covers multiple adhesive areas (for example contact surfaces 507 and/or 505). Alternatively or additional, separate adhesive areas may be covered by separate adhesive liners. In some embodiments, a single handle 532 is used to prepare multiple aspects of the injector (for example to remove adhesive liners from contact surfaces 505 and/or 507 and/or to remove the needle cover). Alternatively or additional, separate handles may be used to prepare separate aspects of the injector.

In some embodiments, an injector includes an adhesive covering a skin contact surface. For example, an adhesive 540 may cover a first skin contact surface 507 on base 502. A separate section of adhesive optionally covers a second skin contact surface 505 on the body (for example on a rear portion of chassis 504). Optionally the adhesive may overhang beyond the edge of base 502 and/or chassis 504. For example, an adhesive skirt may overhang beyond the front and sides of base 502. Optionally the overhang is strengthened by a stiffener 536a, 536b.

In some embodiments, a handle is included for intuitive preparation of the injector. For example, a pull ring handle 532 is connected to a needle cover and/or adhesive liner 534. Handle 532 optionally supplies an intuitive clue to a user that he should remove the needle cover and/or adhesive liner 534 before placing contact surface 507 against the skin. Optionally, the injector includes a lock preventing priming of the injector until handle 532 has been moved (for example until handle 532 has been pulled away from the injector along with the needle cap and/or adhesive liner 534). For example, a skin sensor may be covered and/or locked in a disengaged state (for example extended away from the body) and/or example an activation switch (for example a button 542) may be locked in an inactivated position until handle 534 is pulled away from the injector. In some embodiments, different preparation activities are connected such that a user can perform one action and prepare multiple parts of the injector. For example, the needle cover may connect to an adhesive liner 534 that covers both skin contact surface 507 on base 502 and skin contact surface 505 on housing 530.

Optionally peeling off adhesive liner 534 from both contact surfaces 505 and 507 and removing the needle cover (for example by pulling the needle cover through an opening 503 in base 502) are achieved with one intuitive act of pulling pull ring 532 away from base 502. Alternatively or additionally, a separate adhesive protector may be supplied for each contact surface 505, 507 and/or removing the needle cover may be independent of removing an adhesive protector.

In some embodiments, features on the body facilitate intuitive placement of the injector. For example, the base that is placed on the skin may be the largest flat surface of the injector. Optionally, the top of the injector (opposite the skin contact surface may include a user interface (for example a switch for example button 542 and/or a display for example window 531). A user may intuitively understand that a display and/or button will not be attached against the skin. Optionally sides of the injector that are not placed against the skin will be generally non-flat (e.g. rounded and/or include protrusions and/or indentations).

In some embodiments, opening 503 in base 502 of the device may be large enough to insert and/or remove a sterile needle cover. For example, the width of the opening may range between 1 mm to 2 mm and/or between 2 mm to 4 mm and/or between 4 mm to 10 mm.

Figure 6A:
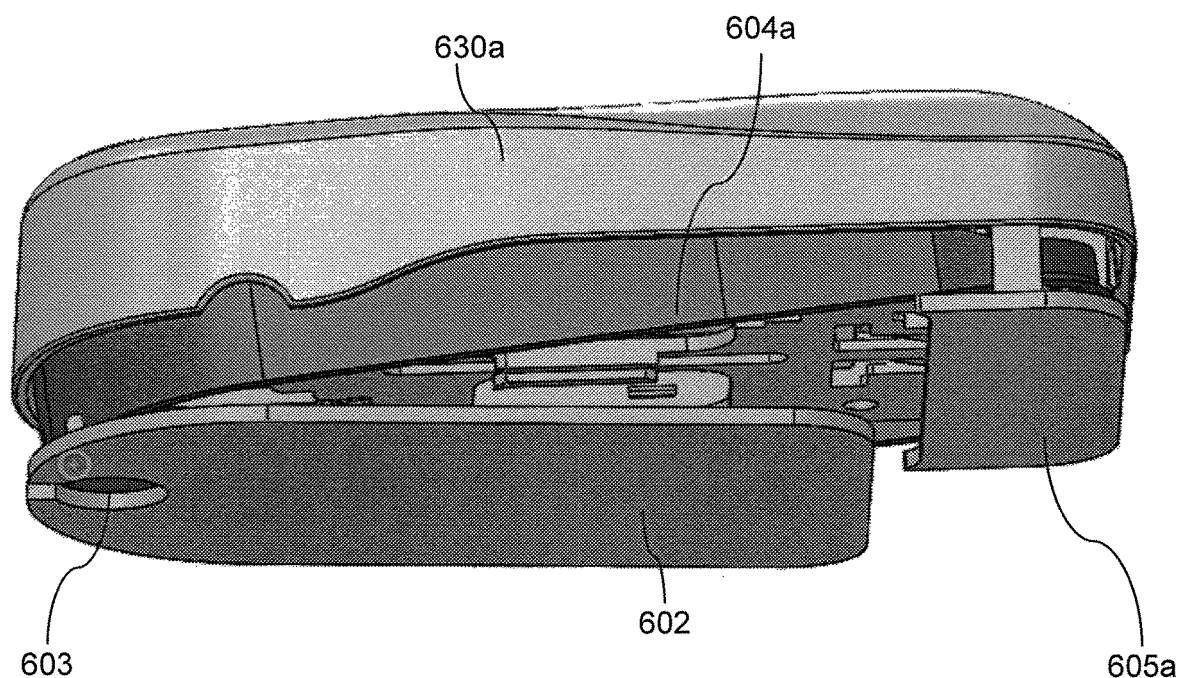
FIGS. 6A-6D are perspective view illustrations of injectors including an insertion and/or retraction mechanism in accordance with embodiments of the present invention.

FIG. 6A is a perspective view of an embodiment of an injector in accordance with an embodiment of the current invention. In some embodiments, an outer housing 630a of an injector includes retaining mechanism, for example a skin contact surface 605a. Optionally, surface 605a includes an adhesive for attaching to the skin of a subject. For example, when the device is active adhesion between surface 605a and the skin of the subject may retain body on the skin and/or retain a base 602 of the injector in a collapsed position next to a chassis 604a.

Figure 6B:
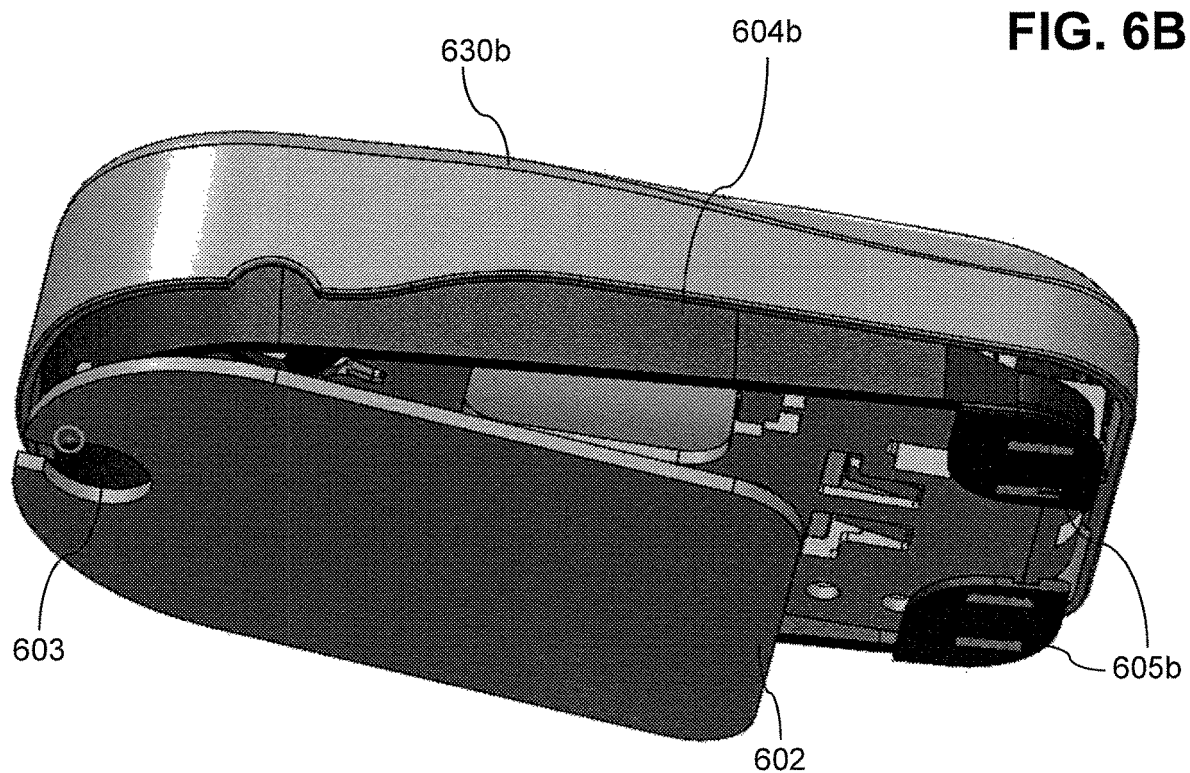

FIG. 6B is a perspective view of an embodiment of an injector in accordance with an embodiment of the current invention. In some embodiments, a chassis 604a of an injector includes retaining mechanism, for example a skin contact surface 605b.

Optionally, surface 605b includes an adhesive for attaching to the skin of a subject. For example, when the device is active, adhesion between surface 605b and the skin of the subject may retain the body on the skin and/or retain a base 602 of the injector in a collapsed position next to chassis 604b.

In some embodiments, when surface 605a or 605b is pulled away from the skin of the user, base 602 may move away from chassis 604a or 604b, causing needle retraction.

In some embodiments, base 602 includes a skin contact surface and/or an adhesive. For example, the adhesive on base 602 may be strong enough to support the injector on an injection site. Optionally, base 602 includes a needle opening 603. For example, when the injector is in an active state, a needle may protrude through opening 603 into an injection site. Optionally, opening 603 is large enough to insert and/or remove a needle cover from a needle when the needle is retracted behind base 603 for example as illustrated in FIGS. 6A and 6B. Optionally, a retaining mechanism may include multiple parts and/or mechanisms and/or attachment surfaces.

In some embodiments base 602 is attached to housing 630a, 630b and/or chassis 604a, 604b via a hinge. For example, the hinge may be near needle hole 603 (e.g. nearer to the front end of the device with the needle hole than the rear end of the device opposite the needle hole). For example, movement of the needle hole may be less than movement of the opposite end of base 602 when base 602 is moved away from chassis 604a, 604b. For example, the location of the center of mass of the needle hole may range between 0 to 10% of the distance between the hinge and the far end of the base and/or between 10 to 30% of the distance between the hinge and the far end of the base and/or between 30 to 50% of the distance between the hinge and the far end of the base and/or between 50 to 80% of the distance between the hinge and the far end of the base and/or FIGS. 6C and 6D are perspective views of embodiments of an injector at the point of needle retraction in accordance with an embodiment of the current invention.

In some embodiments, needle retraction occurs when the skin contact surface 505 of the chassis 504 and/or on a body of the pharmaceutical delivery device lifts off a skin 693 of a subject. Alternately or additionally, in some embodiments the needle retracts while a skin contact surface 505 of the chassis and/or body of the injector is still connected to the skin. For example, the relative movement between the skin contact surfaces of the based 502 and the skin contact surface of the chassis 505 that triggers needle retraction may be more than and/or less than the distance that the skin can stretch to compensate for such movements. For example, the distance of relative movement between the skin contact surface on the base and the skin contact surface on the chassis and/or body of the injector at their closest points may range between 0 to 0.3 mm and/or between 0.3 to 1 mm and/or between 1 mm to 3 mm and/or between 3 mm to 10 mm and/or between 10 mm to 30 mm. Alternatively or additionally, the base may pivot with respect to the body and/or chassis of to the injector to an angle of between 0 to 2 degrees and/or between 2 to 6 degrees and/or between 6 to 12 degrees and/or between 12 to 24 degrees and/or between 24 to 45 degrees when the needle retracts.

Figure 6C:
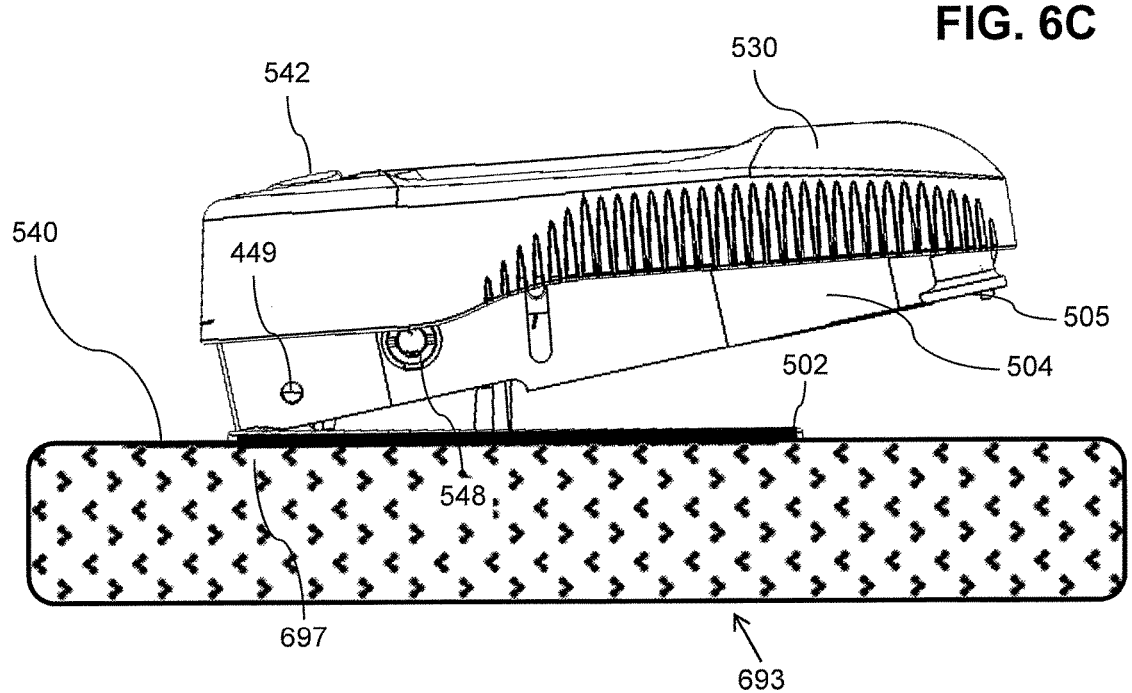
Figure 6D:
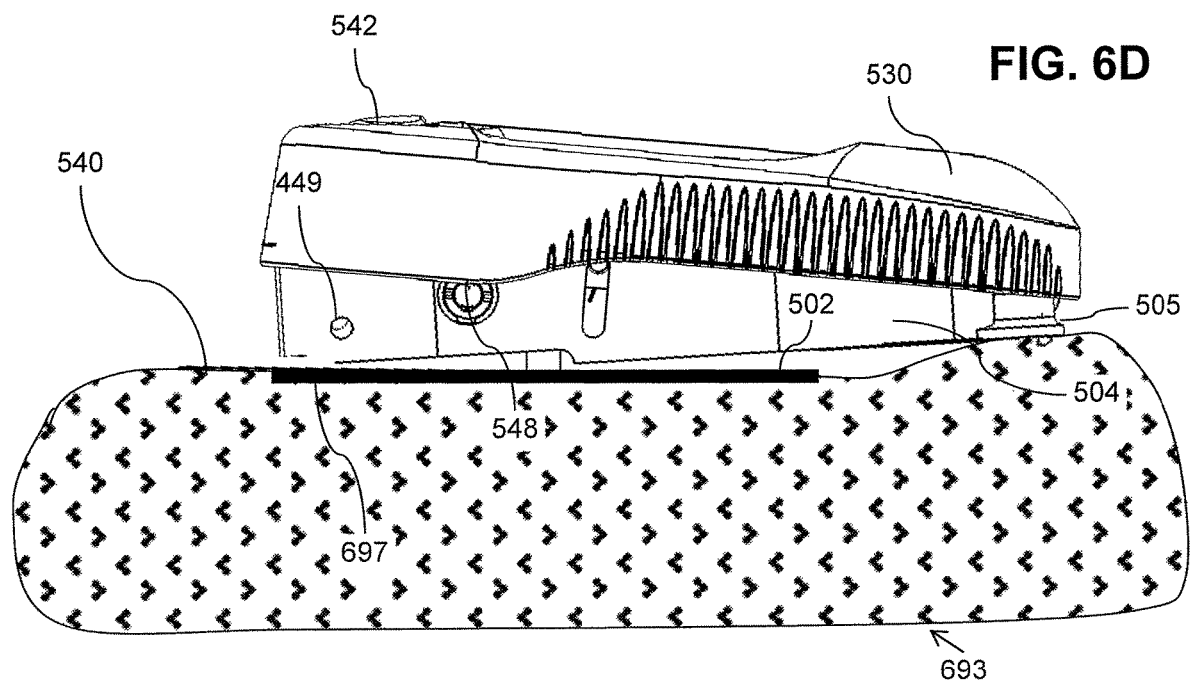

FIG. 6C illustrates embodiment the needle retraction mechanism in which needle retraction occurs when the bass 502 is fully distanced from chassis 504 and/or the skin contact surface 505 of chassis 504 is disconnected from the skin 693 of a subject. For example, the distance between base 502 and chassis 504 at which needle retract occurs may be large enough that while base 502 remains adhered to skin 693, the skin contact surface 505 of chassis 504 raises up off the skin surface. Optionally, when the needle retracts, base 502 is still adhered to the skin 693 around an injection site 697.

For example, in an embodiment in an embodiment where contact surface 505 remains in contact with the skin while the needle retracts, needle retraction may occur when base 502 pivots outward less than 3 degrees and/or less than 5 degrees and/or less than 10 degrees. For example, in an embodiment in an embodiment where contact surface 505 remains in contact with the skin while the needle retracts, needle retraction may occur when the closes points between base 502 and contact surface 505 move between 0 to 0.3 mm and/or between 0.3 to 1 mm and/or between 1 mm to 3 mm and/or between 3 mm to 5 mm relative to one another.

FIG. 6D illustrates an embodiment of an injector where both the skin contact surface of base 502 and the skin contact surface 505 of the chassis 504 remain adhered to the skin when the needle retracts. For example, the needle may retract when the base 502 is only slightly moved with respect to the chassis 504. For example, the relative movement of the skin contact surface on the base 502 and the skin contact surface 505 on the chassis 504 may be small enough when the needle retracts that elasticity of the skin compensates. For example, in an embodiment in an embodiment where contact surface 505 is separated from the skin while the needle retracts, needle retraction may occur when base 502 pivots outward between 5 to 10 degrees and/or between 10 to 20 degrees and/or between 20 to 45 degrees. For example, in an embodiment in an embodiment where contact surface 505 remains in contact with the skin while the needle retracts, needle retraction may occur when the closes points between base 502 and contact surface 505 move between 1 mm to 3 mm and/or between 3 mm to 5 mm and/or between 3 mm to 5 mm and/or between 5 mm to 15 mm relative to one another.

FIGS. 7A-7J are perspective and cut away views of various states of an injector including an exemplary needle insertion mechanism and/or a needle retraction mechanism in accordance with an embodiment of the present invention. Optionally, needle retraction and/or insertion may be driven by a spiral torsion spring and/or a rotary motion drive. For example, movement of the spring may be limited according to a position of the base of the device.

Figure 7A:
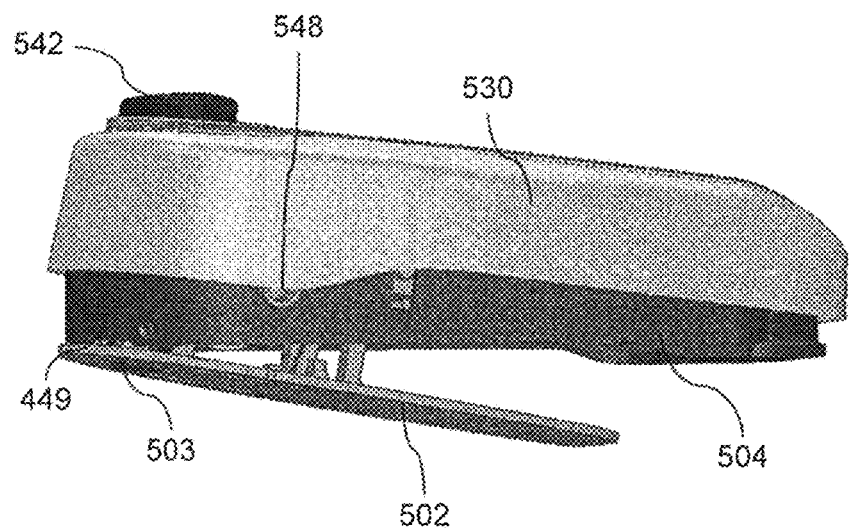
Figure 7B:
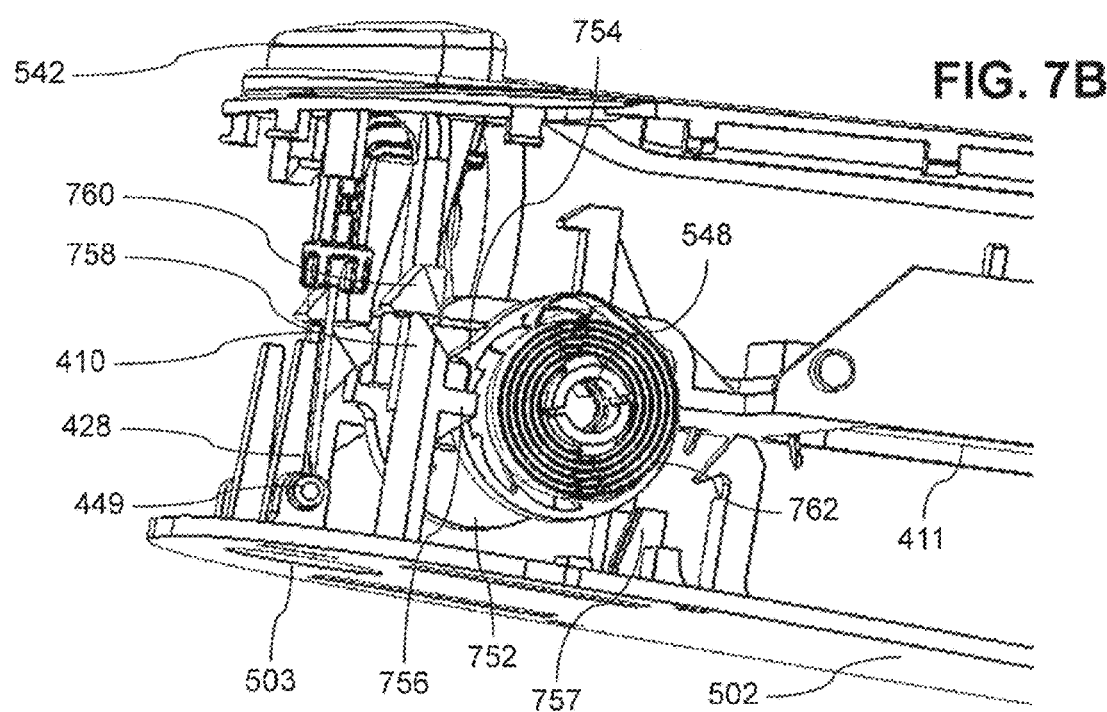

FIGS. 7A and 7B are a perspective and cut away illustrations of a drug delivery device ready to be placed on the skin of a subject in accordance with an embodiment of the current invention. Some external features of the device of FIG. 7A have been describe for example in the description of FIGS. 5A and 5B.

FIG. 7B illustrates a cut away view of an injector in a ready state in accordance with an embodiment of the current invention. In some embodiments, insertion and/or retraction of a needle 410 is driven by a driving wheel 752. In the ready state, drive wheel 752 optionally holds needle 410 in a retracted state. For example, in the ready state, an interference element 756 connected to base 502 of the injector may block movement of a spur 754 on wheel 752 and/or inhibit extension of needle 410.

Optionally wheel 752 rotates around an axis 548.

In some embodiments, a stored energy source impels drive wheel 752. For example, a stored energy source may include a spiral torsion spring 762.

In some embodiments, in the ready state, base 502 may interfere with pushing an activation button 542. For example, while base 502 is extended away from the chassis 504 of the injector, interference element 756 may block movement of an extension 760 of button 542. Optionally, opening 503 is near the pivot 449 of base 502 and/or opening 503 is aligned with needle 410 while base 502 is in the extended position. For example, alignment of needle 410 and opening 503 may allow a needle cover to extend through opening 503.

Optionally base 502 includes a biasing member. For example, member includes an elastic element that is deformed when base 502 is collapsed into chassis 504 and/or forces base 502 into the extended position. For example, member includes a leaf spring that is pushed up against a front wall of chassis 504 when base 502 is collapsed. Alternatively or alternatively, a biasing member may include a coil spring and/or a torsion spring and/or a cushioning element.

Figure 7C:
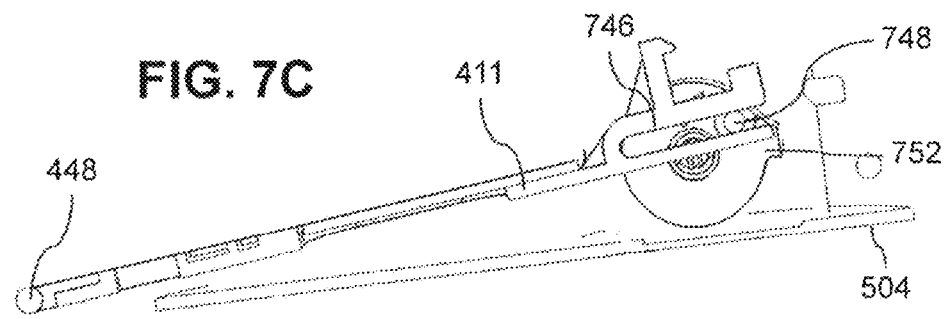

FIG. 7C illustrates a cut away view of a cam drive of an injector in a primed state in accordance with an embodiment of the current invention. In some embodiments, movement of a needle is driven by a rotary drive cam structure including a driving wheel 752 and/or a pin 748 and/or a track 746. For example, a needle assembly may be mounted on a mounting plate 411. Optionally, mounting plate 411 rotates around a pivot 448. Optionally, in the initial needle retracted state, driving wheel 752 is positioned with pin 748 distanced from a skin contact surface of the injector (for example in the primed state (when base 502 is optionally collapsed into chassis 504)), the skin contact surface may include an outer surface of base 502 and chassis 504.

Optionally, in the primed state, pin 748 holds track 746 and/or mounting plate 411 and/or needle tip 428 in a retracted position behind the skin contact surface.

FIG. 7C' illustrates a perspective external view of an injector in a primed state in accordance with an embodiment of the current invention. Optionally in the primed state, base 502 is collapsed against chassis 504. For example, collapsing may be caused by pushing the injector against an injection site. For example, base 502 and the bottom surface of chassis 504 may be held flush against the surface of the injection site. For example, base 502 may be attached to the injection site by an adhesive 540. For example, a skirt of adhesive 540 may by unattached to base 502.

FIG. 7D illustrates a cutaway view of an injector in a primed state in accordance with an embodiment of the current invention. In some embodiments, in the primed state, element 758 may no longer inhibit pushing of activation button 542. For example, element 758 may be positioned such that a sloped surface of extension 760 of button 542 contacts element 758 such that pushing button 542 pushes element 758 out of the way of extension 760. Optionally, pushing button 542 pushes element 758 out of the way of spur 754 of wheel 752 and/or frees wheel 752 to turn to its active position and/or drive needle tip 428 out through opening 503 for example as illustrated in FIG. 7E.

Alternatively or additionally, movement of base 502 may directly cause element 758 to move out of the way of spur 754 of wheel 752. For example, of needle tip 428 may extend immediately upon collapse of base 402 toward chassis 404 without the user pushing a button. Alternatively or additionally, needle tip 428 may be extended manually, for example, by a force of the user pushing housing 530 and/or a button 542 towards the injection site, for example, needle extension may not be powered by a stored energy source in the injector.

Figure 7E:
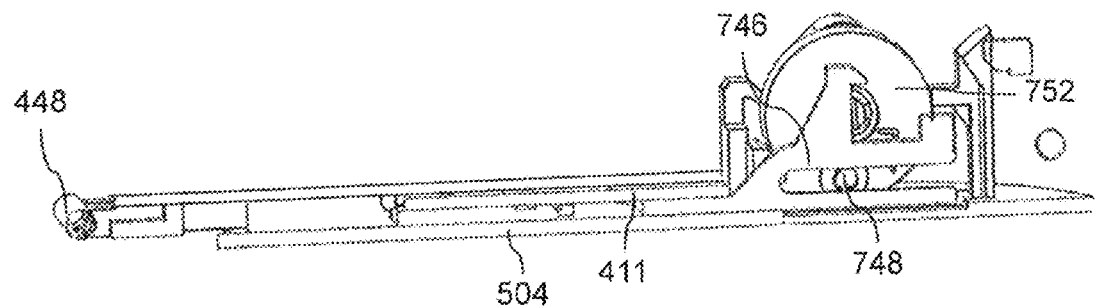
Figure 7E:
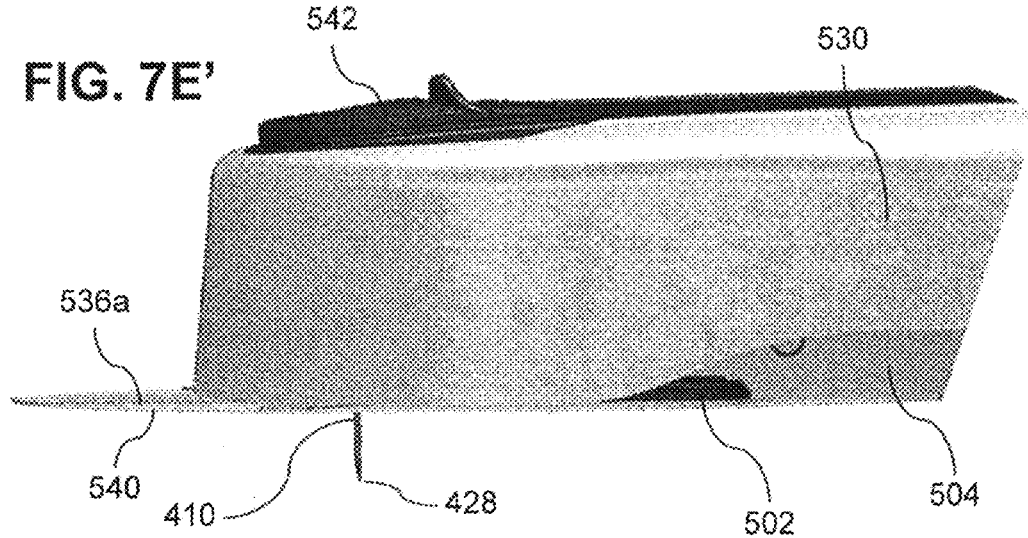

FIG. 7E is a cutaway view of a needle driver in an activated state in accordance with an embodiment of the current invention. Optionally in the active state, wheel 752 has been rotated by spring 762 until pin 748 is positioned close to the skin contact surface of base 502 and/or chassis 504. Optionally, pin 748 drives track 746 toward the skin contact surface and/or drives mounting plate 411 towards the skin contact surfaces and/or drives needle tip 428 out opening 503 to an extended position (for example as illustrated in FIGS. 7E' and 7F).

FIG. 7E' is an exterior perspective view of an injector in an active state in accordance with an embodiment of the current invention. Optionally, in the active state needle tip 428 is extended out opening 503. For example, base 402 is collapsed into chassis 404 and/or housing 530 such that skin contact surfaces of base 402 and/or chassis 404 and/or housing 530 are flush. For example, the contact surfaces may be in contact with and/or adhere to a skin surface of the user.

Figure 7F:
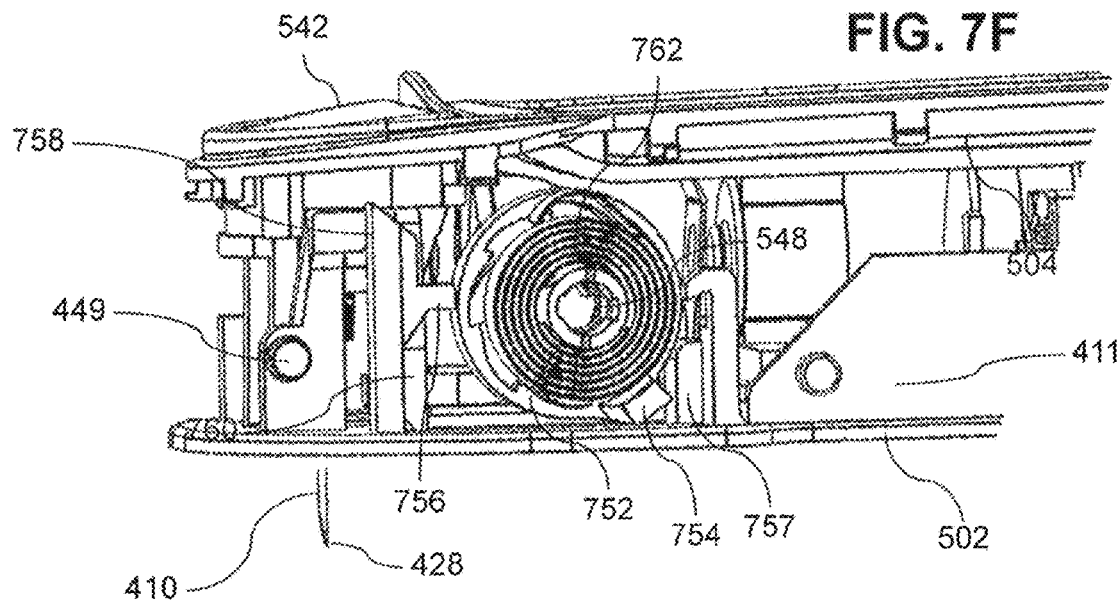

FIG. 7F illustrates a cutaway view of a needle driver and base in an active state in accordance with an embodiment of the current invention. For example, in the active state an interference element 757 on base 502 may block spur 754 and/or inhibit further rotation of wheel 752. Further rotation of wheel 752 would move pin 748, plate 411 and/or needle tip 428 upward away from the skin contact surfaces. Blocking further rotation optionally, locks pin 748, plate 411 and/or needle tip 428 in the extended position.

Figure 7G:
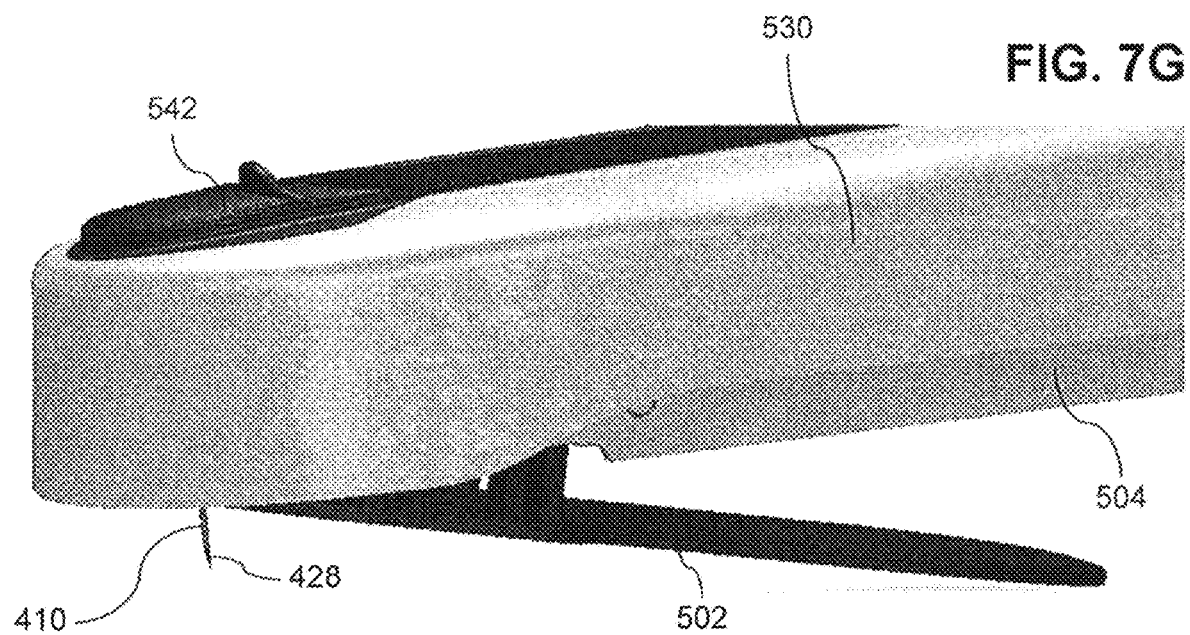

FIG. 7G is an external perspective view of an injector in the process of removal from an injection site in accordance with an embodiment of the current invention. In some embodiments, pulling housing 530 away from an injection zone, causes base 502 to extend outward from chassis 504. For example, base 502 rotates around pivot 449 with respect to chassis 504.

In some embodiments, in the primed state, opening 503 is aligned with needle 410 such that movement of mounting plate 411 towards chassis 504 and/or base 502 extends needle tip 428 out opening 503.

Figure 7H:
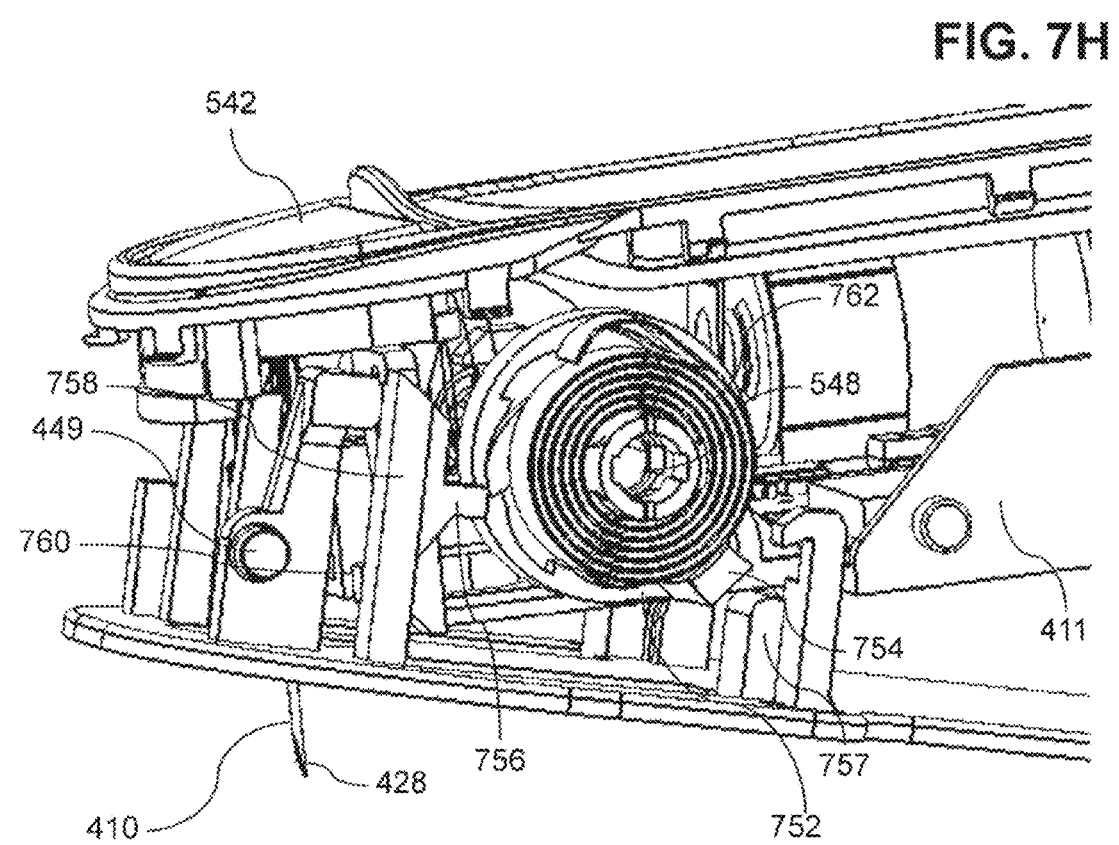

FIG. 7H is a cutaway view of a needle driver of an injector in the process of removal from an injection site in accordance with an embodiment of the current invention. Optionally, moving base 502 away from chassis 504 disengages interference element 757 from spur 754. For example, once freed of interference element 757, wheel 752 turns a half rotation moving pin upward to a position distanced from the skin contact surface of plate 411 and/or chassis 504 and/or base 502. Moving pin away from the skin contact surfaces optionally rotates plate 411 away from chassis 504 and/or retracts needle tip 428 through opening 503 and/or up behind the skin contact surface of base 502 and/or chassis 504 and/or body 530.

Figure 7I:
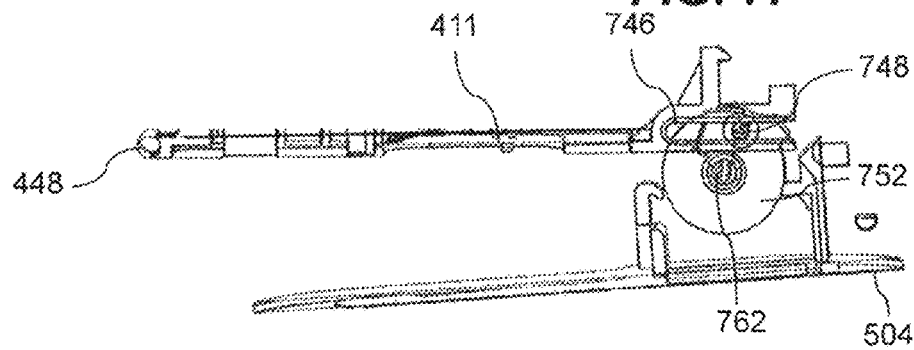
Figure 7I:
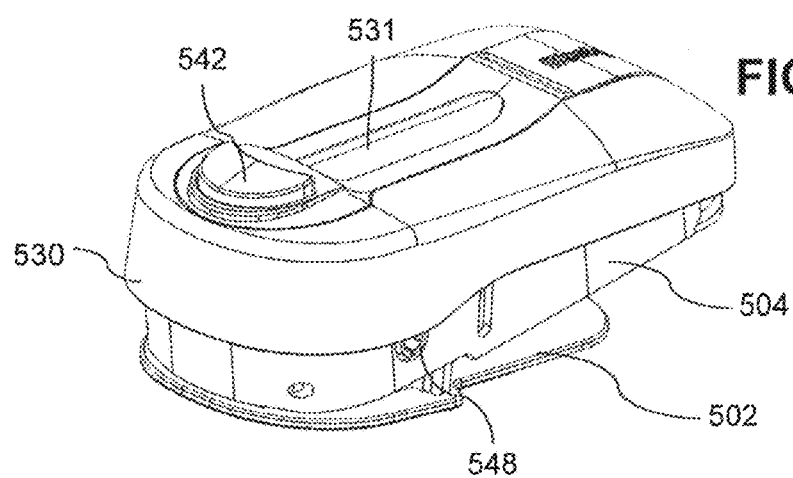
Figure 7J:
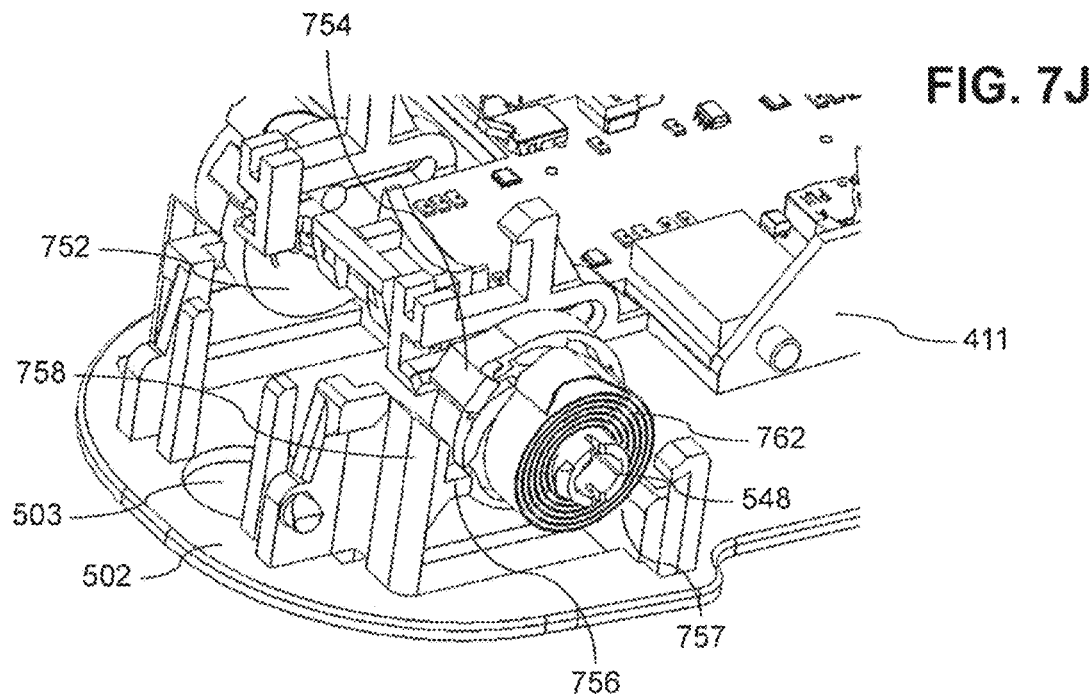

FIG. 7I illustrates a driver of an injector in a protected state in accordance with an embodiment of the current invention. Optionally, during retraction, wheel 752 is rotated by spring 762 until pin 748 just passes the point furthest from the skin contact surfaces of base 502. Optionally, during retraction, wheel 752 is rotated by spring 762 until pin 748 almost reaches its preinjection position (for example as illustrated in FIG. 7C). For example, a stop prevents further movement of wheel 752. Optionally, needle tip 428 is locked retracted by the stop of wheel 752 (preventing wheel 752 from going forward) and/or by spring 762 (prevent wheel from going backward) and/or because a downward force pushed wheel 752 into the stop. In some embodiments, needle 410 remains aligned with opening 503 after retraction. For example, locking of needle 410 in the retracted position prevents a stick hazard regardless of the alignment between needle 410 and opening 503.

FIGS. 7I' and 7J illustrate an external perspective view and a cutaway internal view respectively of an injector in a protected state in accordance with an embodiment of the current invention.

In some embodiments, base 502 is biased outwards, away from chassis 504. For example, even if somehow base 502 is peeled off the injection site without opening, biasing will cause base 502 to open and/or retract needle tip 428. Alternatively or additionally, a base may rotate freely without biasing and/or the base may be biased inward (toward the chassis). For example, when the body is pulled away from the injection site, the adhesive may pull the base away from the body and/or cause needle retraction. Alternatively or additionally, the needle may not retract with respect to the body. For example, when the base extends away from the body it may extend outward past the needle tip and/or shield the needle tip, for example to prevent a stick hazard.

Adhesive Structure

Figure 8:
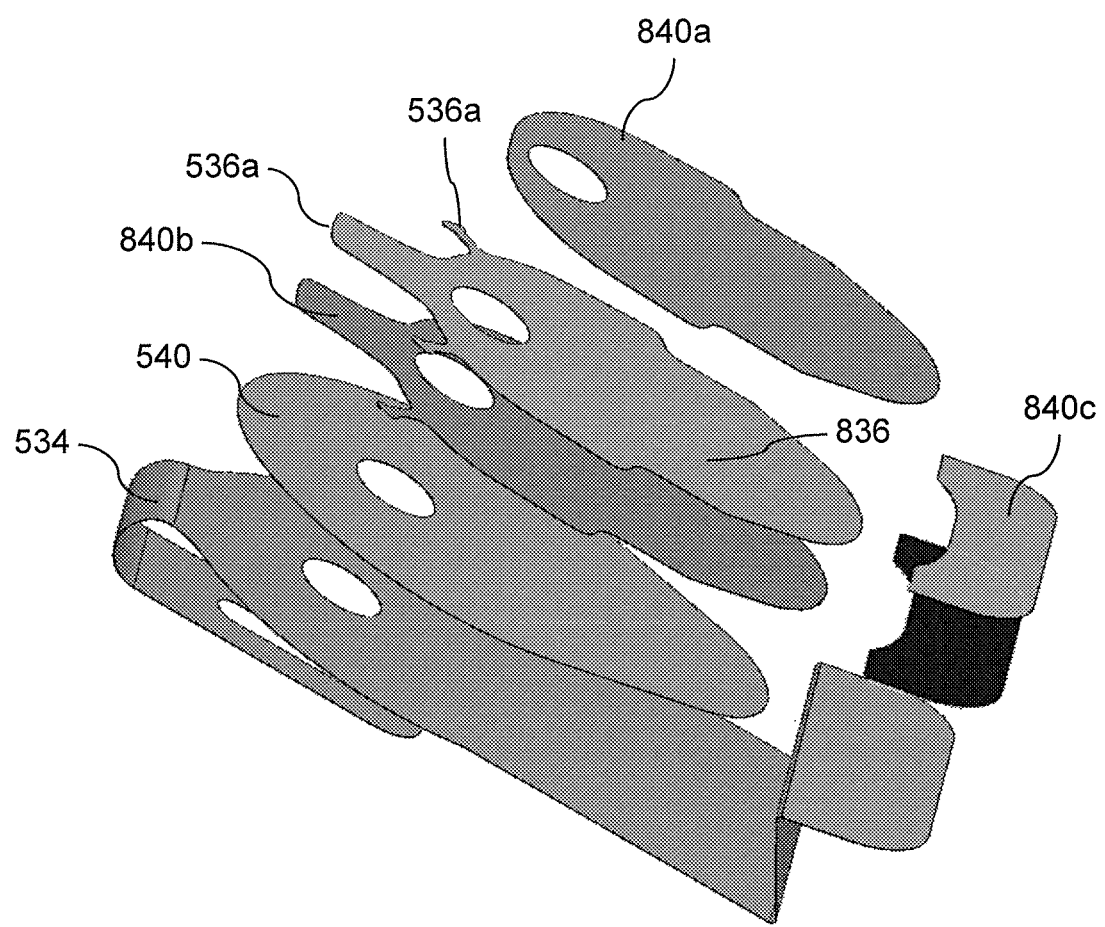
FIG. 8 is an exploded view of an adhesive structure in accordance with an embodiment of the present invention.

FIG. 8 is an exploded view of an adhesive structure in accordance with an embodiment of the present invention. Optionally, skin adhesive 540 includes a flexible substrate with an adhesive on one side. An optional adhesive layer 840b connects the flexible substrate of adhesive 840b to a stiffener 836. Part of stiffener 836 is attached to base 502 by an adhesive layer 840a. Optionally, part of stiffener 836 and/or part of the substrate of adhesive 540 forms a skirt. For example, part of the skirt may overhang beyond base 502 and/or part of the skirt may underlie base 502, but not be attached thereto. In some embodiments, a second adhesive is connected to the housing and/or chassis of the device. For example, a double sided adhesive 840c may be attached to contact surface 505 of chassis 504. Optionally a protective liner 534 covers skin adhesives 540 and/or 840c. In some embodiments, liner 534 is peeled off before use of the injector. Optionally liner 534 may be interconnected to a sterile needle cap.

Optionally the needle cap and liner 534 may removed and peeled off together.

Alternatively or additionally, an adhesive structure may have a different number of parts and/or layers.

Stabilized Injector

Figure 9A:
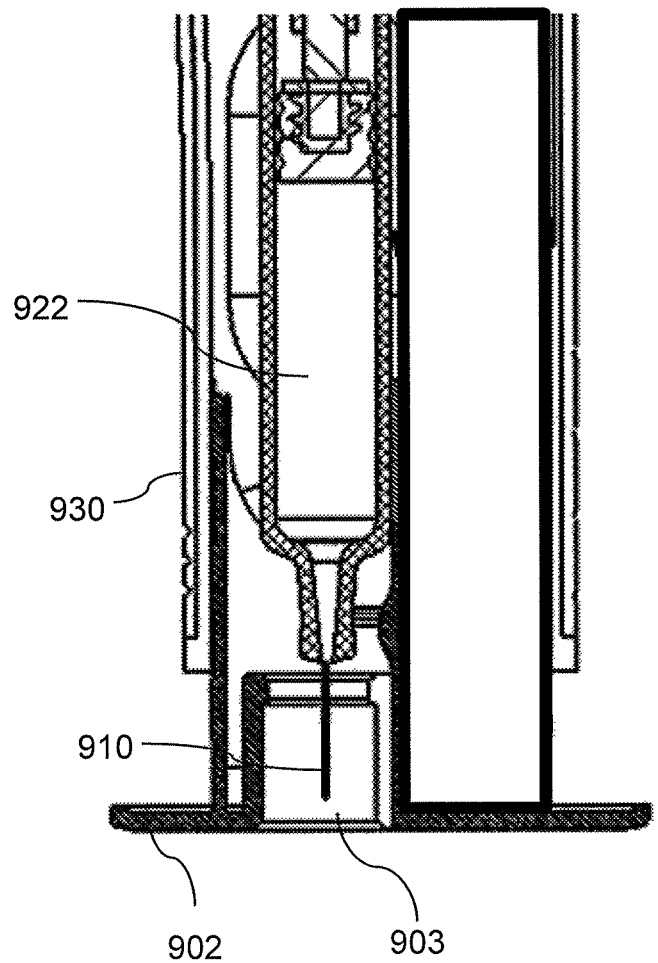
FIGS. 9A-9C are schematic diagrams an injector in accordance with an embodiment of the present invention.
Figure 9B:
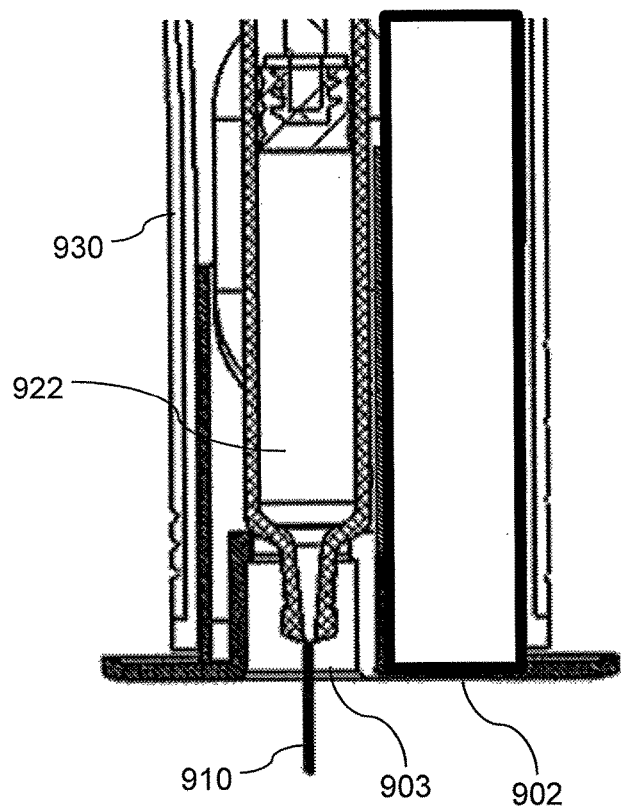
Figure 9C:
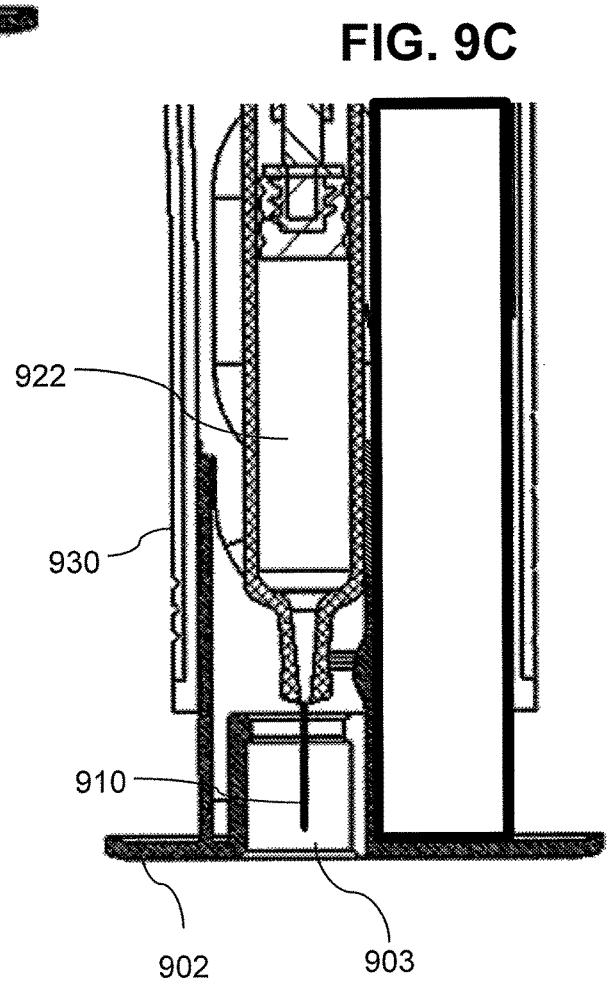

FIGS. 9A-9C are schematic cross sectional diagrams a stabilized pen injector in accordance with an embodiment of the present invention.

FIG. 9A illustrates a stabilized injector in a ready state in accordance with an embodiment of the current invention. Optionally, a standard syringe 922 with a straight needle 910 is mounted behind an adhesive base 902. Optionally, the injector is supplied with a sterile needle cap. For example, the needle cap may be removed through an opening 903 in base 902 before starting injection. To start injection a user optionally adheres base 902 to an injection site and/or pushes a housing 930 of the injector towards the injection site. For example, the pressure applied by the user may collapse base 902 towards housing 930 such that needle 910 protrudes through opening 903 into the injection site.

FIG. 9B illustrates a stabilized pen injector in an active state in accordance with an embodiment of the current invention.

In some embodiments, base 902 is retained in a collapsed state, for example, base 902 may be biased towards housing 930. Alternatively, a retaining and/or locking mechanism retains base 902 in the collapsed state. Optionally, an actuator delivers a drug through needle 910 into the subject while the adhesive retains the device on an injection site and/or while the device is retained in the active state.

In some embodiments, a user may pull housing 930 away from an injection site (for example at the end of drug delivery and/or before the end of drug delivery). For example, pulling housing 930 away from an injection site while base 902 remains adhered to the injection site overcomes a retaining mechanism and/or deploys a shield, for example by extending base 902 to a protecting state.

FIG. 9C illustrates a stabilized pen injector in a protected state in accordance with an embodiment of the current invention. For example, when base 902 is deployed from an active state to an extended state, it may permanently lock impeding access to needle 910 and/or preventing a needle stick injury.

In alternative embodiments, a stabilized pen injector optionally includes a needle insertion and/or retraction mechanism. For example, the insertion and/or retraction may perform insertion and/or retraction via an actuator and/or a stored energy source that is triggered for example by extending and/or collapsing base 910.

Alternative Patch Needle Mechanism

FIGS. 10A-10F are a schematic diagrams of a needle injection/retraction mechanism in accordance with an embodiment of the present invention. In some embodiments, a needle may be inserted and/or retracted by a linear movement mechanism. Optionally, the mechanism may be powered by a stored energy source, for example a coil spring.

Figure 10A:
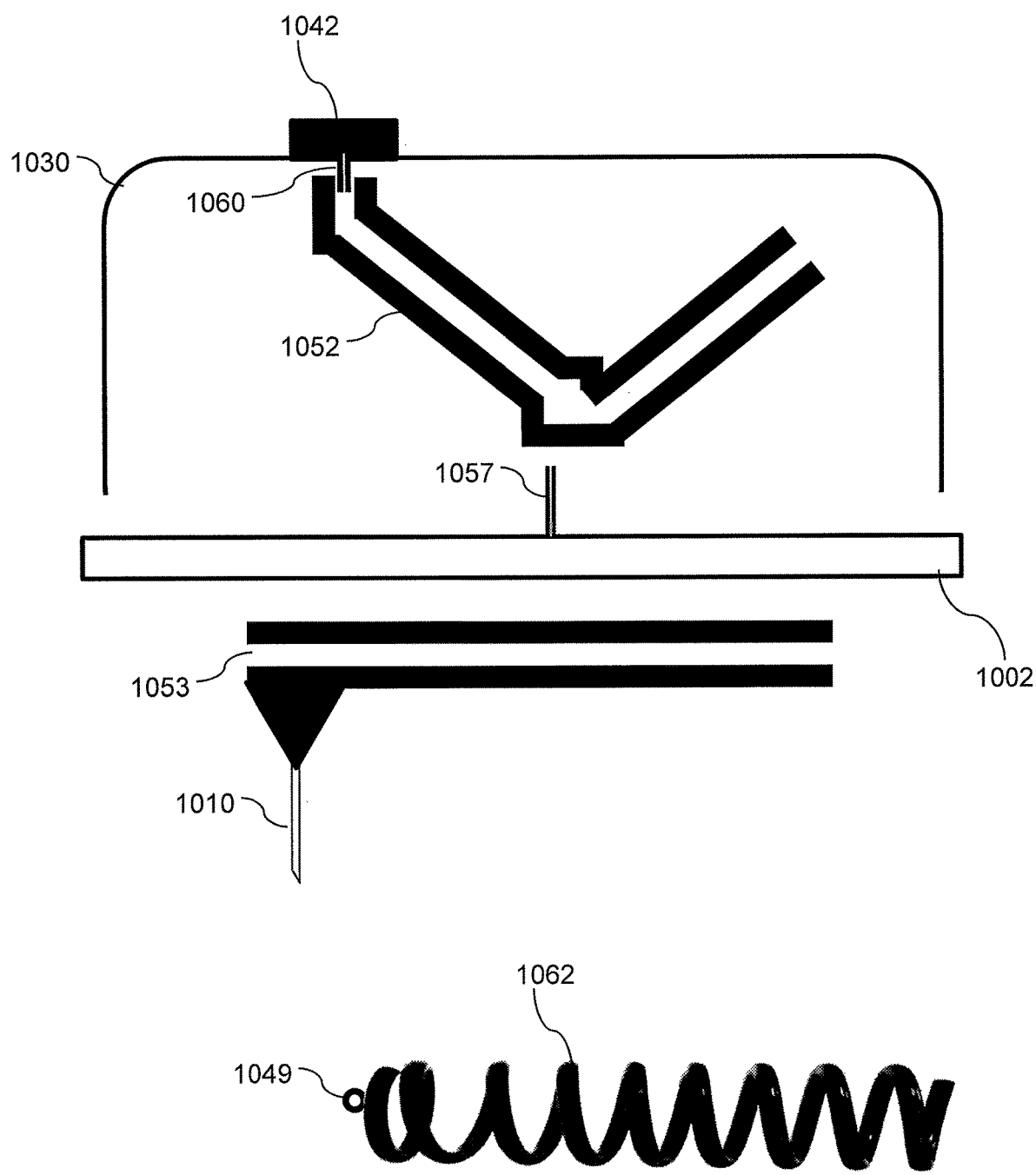
FIGS. 10A-10F are schematic diagrams of various states of injector in accordance with an embodiment of the present invention.

FIG. 10A is an exploded view of a needle injection/retraction mechanism in accordance with an embodiment of the present invention. In some embodiments, a mechanism may include an activation button 1042, a housing 1030, a base 1002 movably attached housing 1030, a fixed track 1052, a vertically movable track 1053 attached to a needle 1010, interference elements 1060 and 1057 (e.g. attached to button 1042 and base 1002 respectively), a pin 1049 attached to a coil spring 1062 stored energy source. For example, spring 1062 pulls pin 1049 rightward in the exemplary embodiment of FIGS. 10A-F.

Figure 10B:
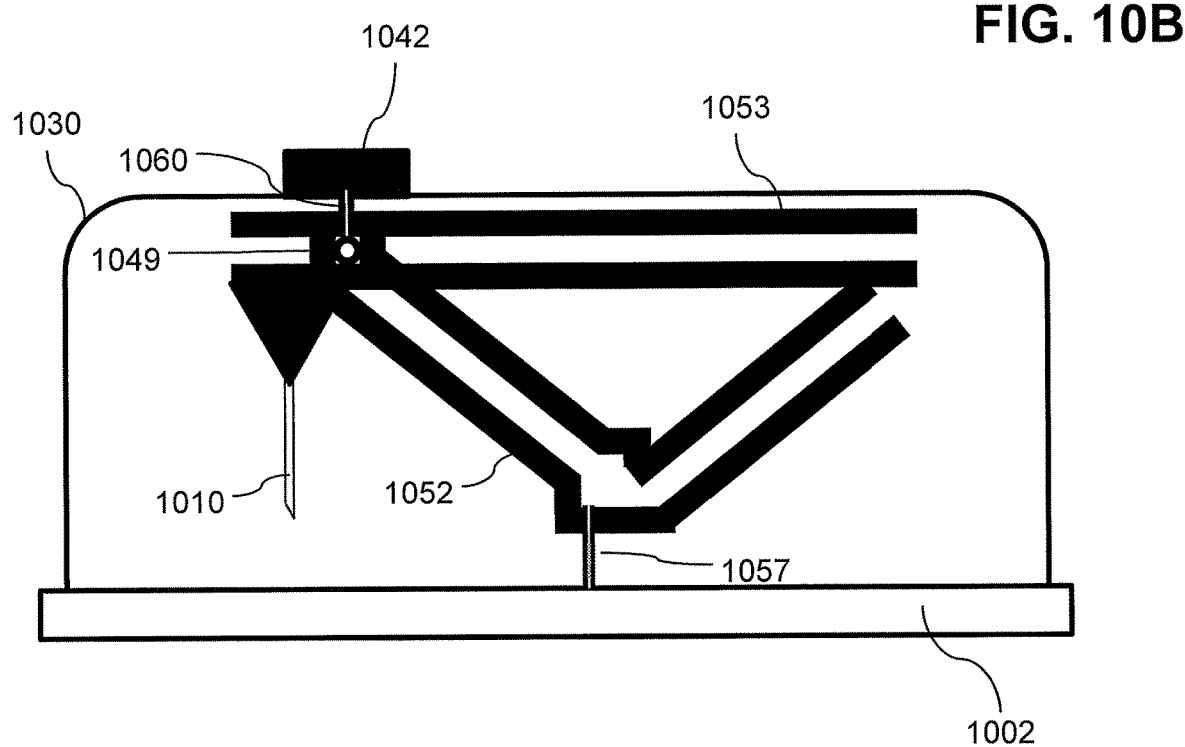

FIG. 10B illustrates a needle mechanism before placement on an injection site.

Optionally, before placement of the device, pin 1049 is prevented from moving to the right by a vertical portion of the wall of track 1052. Needle 1010 is optionally retracted upward and/or base 1002 is optionally extended downward.

Figure 10C:
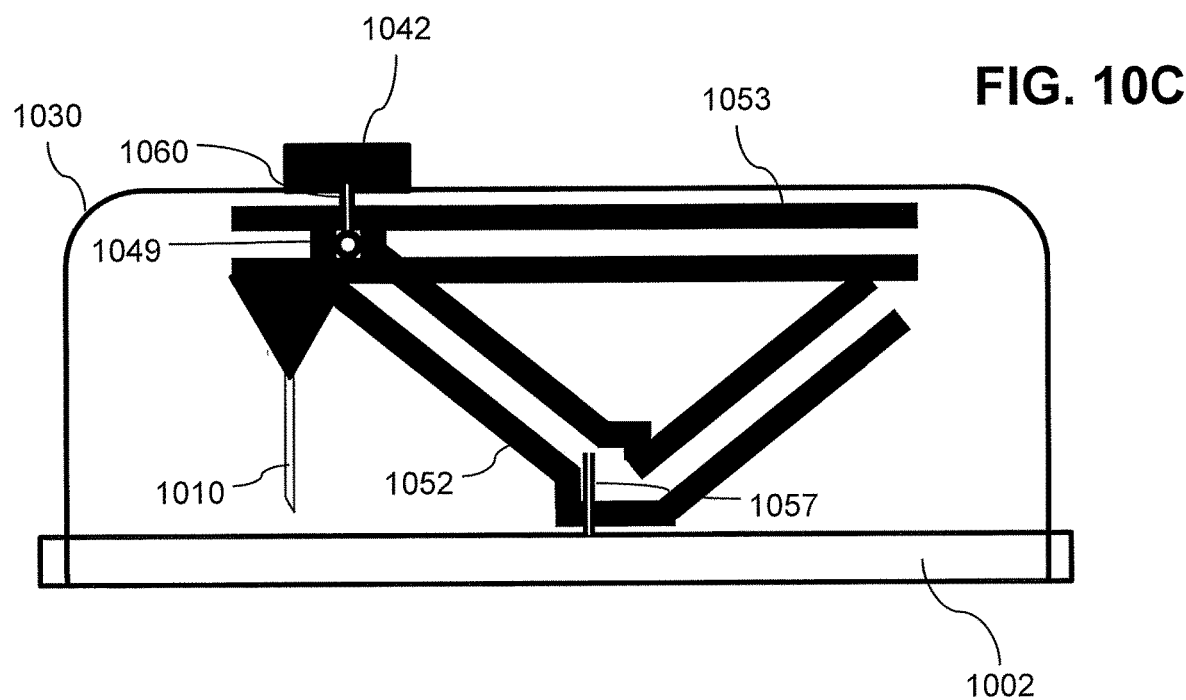

FIG. 10C illustrates a needle mechanism in a primed state after placement on an injection site in accordance with an embodiment of the present invention. Optionally, placement of the device on the injection site pushes up base 1002 and causes interference element 1057 to block the lower part of track 1052.

Figure 10D:
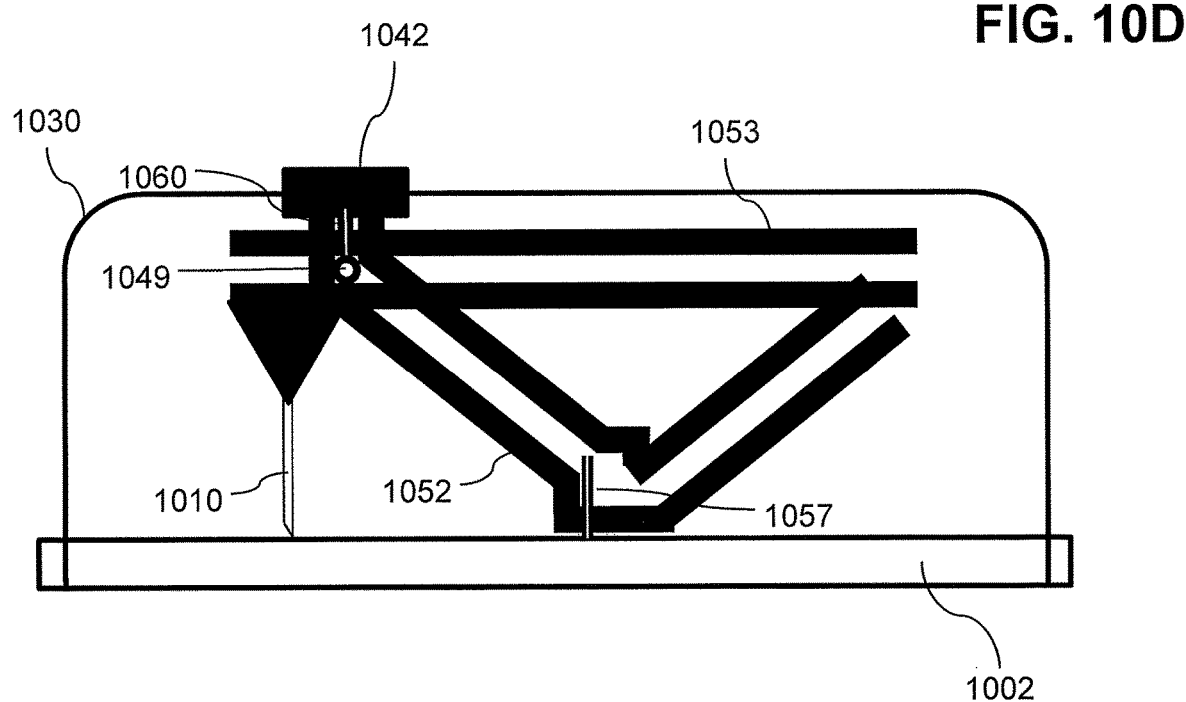
Figure 10E:
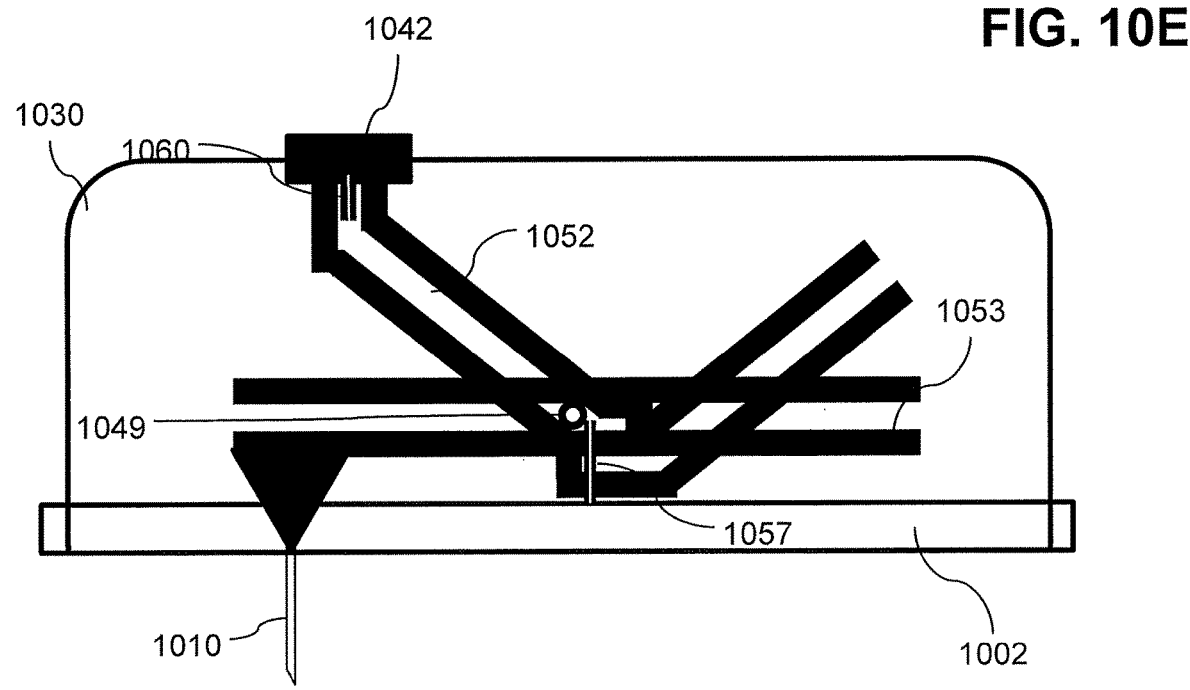

FIG. 10D illustrates a needle mechanism at the moment of depressing activation button 1042 in accordance with an embodiment of the present invention. Optionally, depressing button 1042 pushes interference element 1060 downward and/or pushes pin 1049 downward from the vertical part of track 1052 to a sloped portion of the track 1052. The rightward force of spring 1062 pulls pin 1049 against the sloping wall of track 1052.

FIG. JOE illustrates a needle mechanism in an active state in accordance with an embodiment of the present invention. Pin 1049 is optionally pulled by rightward along track 1052. For example, as pin 1049 moves rightward, it moves downwards and/or pushes track 1053 downward and/or pushes needle 1010 out an opening in base 1002 into an extended position and/or into the injection site. Optionally, rightward motion of pin 1049 is stopped and/or needle 1010 is locked in the extended position when it contacts interference element 1057.

Figure 10F:
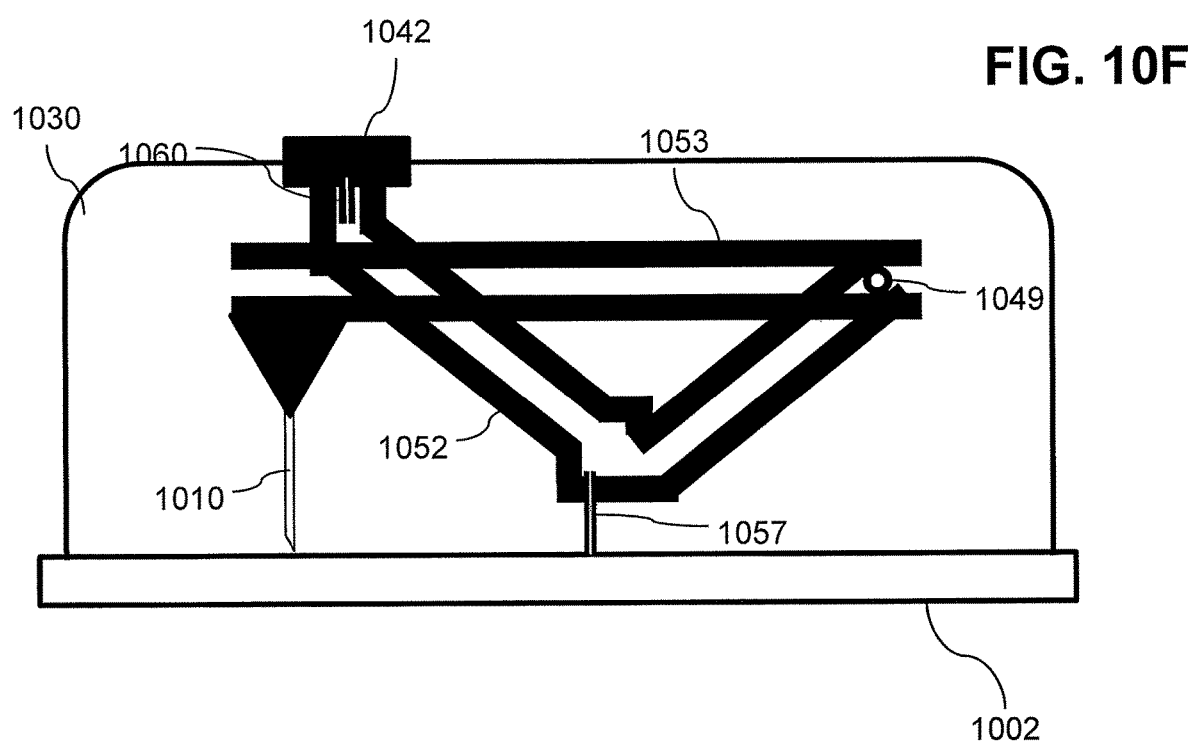

FIG. 10F illustrates a needle mechanism in a protected state in accordance with an embodiment of the present invention. Optionally the device is removed from the injection site by pulling housing 1030 away from the injection site. Base 1002, which is optionally adhered to the injection site, is optionally held to the injection site such that housing 1030 is pulled upwards with respect to base 1002. Optionally movement of housing 1030 with respect to base 1002 moves interference element 1057 out of track 1052. Once element 1057 has moved out of track 1052, pin 1049 is optionally freed to move rightward up track 1052. As pin 1049 moves rightward and upward, track 1053 and/or needle 1010 are pulled up into the retracted and/or protected position.

Exemplary Dimensions of a Drug Delivery Device

In some embodiments the payload of a reservoir (for example a syringe) may include, for example between 0.5 and 2 ml and/or between 2 and 7 ml and/or between 7 and 6 ml and/or between 7 and 10 ml of a drug and/or more. In some embodiments, the injector may discharge the entire payload as a single dose. A drug delivery device may include, for example, a patch injector, and/or an internally powered driver to drive the plunger and/or discharge the payload.

For the sake of this application, an internally powered injector driver may be defined as a drive mechanism powered by energy stored at least temporarily within the injector. Power may be stored in a power supply, for instance as chemical potential (for example a chemical that produces an expanding gas and/or a battery) and/or mechanical potential (for example stored in an elastic member and/or a spring and/or a pressurized gas). For example, the driver may be designed to discharge the payload over a time period ranging between 20 and 120 seconds and/or between 120 and 600 seconds and/or between 600 seconds and an hour and/or between an hour and a day and/or longer.

In some embodiments, the apparatus may be preprogrammed to wait a fixed time delay ranging between 2 to 20 minutes and/or 20 minutes to an hour and/or an hour to 6 hours and/or 6 hours to 2 days after activation before beginning delivery of the substance. Optionally the length of the time delay may be an estimated time for a temperature sensitive component of the apparatus to reach a preferred working temperature. For example, the temperature sensitive component may include the drug and/or a battery.

In general, discharge may be driven by a driver. An internally powered driver may be powered by various mechanisms including for example a motor as discussed, including for example a DC motor, an actuator, a brushless motor, and/or a transmission including for example a telescoping assembly and/or a threaded element and/or a gear and/or a coupling and/or an elastic mechanism (for example a spring and/or a rubber band) and/or an expanding gas and/or a hydraulic actuator).

A drug delivery device in accordance with some embodiments of the present invention may include a reservoir part as discussed. For example, a reservoir may include a medicine container and/or a syringe. Optionally a syringe may be preloaded with medicine using standard equipment and/or in an aseptic room. A preloaded syringe may optionally include a proximal opening. A plunger may optionally seal the proximal opening and/or protect the sterility of the contents of the syringe. A sterile needle, typically hollow, may optionally be connected to the syringe barrel. For example, the hollow of the needle may be in fluid communication with the interior of the barrel.

The needle may optionally be rigidly attached to the extension at the distal end of the barrel. The sterility of all and/or part of the needle may for example be protected by a protective cap. The protective cap may remain on the needle when the syringe is supplied and/or installed into an injector. For example, the medicine container may optionally include a cylindrical barrel rigidly attached to a needle. In some embodiments, a plunger may slide axially along the inside of the barrel to discharge a medicine payload. For example, the medicine may be discharged through the hollow needle. The protruding tip of the needle may be oriented at an angle to the axis of the barrel.

An aspect ratio of the base may be defined as the ratio of the length of the longest axis of the base to the shortest axis. Optionally the axis ratio may range between 1 to 1.5 and/or 1.5 to 2 and/or between 2 to 3 and/or greater than 3. In some embodiments, the height of the injector may range between half the length of the short axis of the base to the length of the short axis of the base and/or between the length of the short axis of the base to twice the length of the short axis of the base and/or greater than the twice length of the short axis of the base. The height of the injector may supply leverage for pivoting the adhesive off the skin of a patient after use.

In some embodiments, the force to insert the needle to the skin of a patient may range for example between 0.02 to 0.2 N and/or between 0.2 and 0.5 N and/or between 0.5 to 5 N. Optionally, the force required to inject the drug (for example the force on a syringe plunger) may range for example between 5 to 60 N. For example, the force required to inject the drug may depend on the injection rate and/or the viscosity of the drug and/or the syringe geometry and/or the needle dimensions.

In some embodiments, a needle protection mechanism may be triggered by a linear force greater than, for example, between 10 to 60 N.

For example, drug delivery device may include an auto-injector. The auto-injector may be activated by manually pushing with enough force to insert the needle. The device may then apply an injection force to inject a drug. Once the entire drug is injected and/or when there is an obstruction and/or occlusion, the injection force may rise until it passes a threshold triggering safeguarding of the needle and/or ending injection.

For example in the event of an occlusion and/or at the end of delivery, the linear force generated by the device may increase to the level of up to 60 N. A needle safeguarding mechanism (for example a needle retraction mechanism) may be sensitive to the force. For example, the mechanism may include a snap that gives way at 70 N returning the needle to the retracted position.

In some embodiments, the stress to inject a medicine and/or to trigger safeguarding of a needle may include a torque. For example, injection of medicine may be driven by a plunger. The plunger may optionally be driven by a threaded assembly, for example a threaded screw and/or teeth and/or a telescoping assembly. Optionally the pitch of the teeth and/or an associated screw may range for example between 0.5 and 2 mm. The diameter of the screw may range for example between 2.5 and 15 mm. The torque to power injection may range for example between 0.2 and 1.0 N*cm. The trigger torque (the torque at which the needle safeguarding is triggered) may range for example between to 0.5 to 2 and/or from 2 to 7 and/or from 7 to 10N*cm.

During injection, the linear movement of a plunger may range for example between 10-50 mm. The length of movement of the plunger may vary for example with the volume of medicine to be injected that may range for example between 0.5 to 3 ml.

In some embodiments, a safeguarding mechanism may be sensitive to a torque. For example, the needle may be retracted when the mechanism is exposed to a twisting moment. Optionally, discharge may be driven by a torque. For example, the driver may apply torque to threaded element pushing a plunger. When the torque on the driver reaches a threshold value, the needle may be released and/or retracted and/or a needle shield may be deployed. Alternatively or additionally, the trigger mechanism may require both a torque and a linear force. For example, requiring both a torque and a linear stress may prevent premature activation due to momentary friction.

In some embodiments a time of discharge may range may depend on the fill volume and/or viscosity For example the expected injection speeds may be Injection speed depend on viscosity, for example for viscosity ranging from 1 cp to 15 cp the expected injection rage may range between 30 to 70 sec/1 ml, for example for viscosity ranging from 15 cp to 60 cp the expected injection rate may range between 35 to 60 sec/ml for viscosity above 60 cp the expected injection rate may range between 53 to 67 sec/1 ml. The maximum and/or minimum expected injection time may for example be the maximum and/or minimum allowed fill volume divided by an injection rate.

For example an expected time of discharge may range for example between 24 to 78 seconds (for example for between 0.8 and 1.2 ml of fluid having a viscosity ranging between 1 to 15 cp) and/or between 36 to 68 seconds (for example for between 1.2 and 1.7 ml of fluid having a viscosity ranging between 1 to 15 cp) and/or between 51 to 92 seconds (for example for between 1.7 and 2.3 ml of fluid having a viscosity between 1 to 15 cp) and/or between 70 to 150 seconds (for example for 2.0 to 2.5 ml of fluid having a viscosity of between 15 and 70 cp) and/or between 120 seconds and 3 minutes for larger volumes and/or viscosities. In some embodiments, injection times may be longer. The length of the injection time may be determined by considerations other than viscosity and/or volume.

In some embodiments, the reservoir may have a length ranging for example between 20 and 72 and/or 72 and 78 mm and/or 78 and 80 mm and/or 80 and 200 mm. In some embodiments an internal cylindrical space of a reservoir may have an average width ranging for example between 1 and 3 mm and/or 3 and 10 and/or 10 and 15 mm and/or 15 and 25 mm and/or 25 and 50 mm. Optionally a reservoir may have a circular cross section such that width is the diameter of the circle. In some embodiments, an extension may have a straight end portion with a length ranging for example between 1 and 3 mm or 3 and 7 mm or 7 and 8 or 8 and 10 mm or 10 and 15 mm or 15 and 50 mm. In some embodiments, the exposed straight portion of a needle may have a length ranging for example between 1 and 5 mm or 5 and 7 mm or 7 and 10 mm or 10 and 20 mm.

In some embodiments, an extension may have a sealing ring for a needle cap. The sealing ring may have a length ranging for example between 0.1 and 0.6 mm or 0.6 and 1 mm or 1 and 2.5 mm or 2.5 and 3 mm or 3 and 6 mm or 6 and 15 mm. In some embodiments a sealing ring may have an internal cavity with a length ranging for example between 0.5 and 1.5 mm/or 1.5 and 2.5 mm or 2.5 and 5 mm or 5 and 10 mm.

In some embodiments the sealing ring may have an external average width which may also be an average outer diameter ranging for example between 1 and 7 mm or 7 and 5 mm or 5 and 10 mm or 10 and 20 mm. In some embodiments the sealing ring may have an internal average width which also may be an average inner diameter ranging for example between 1 and 3 mm or 3 and 7 mm or 7 and 10 mm or 10 and 18 mm. In some embodiments, the extension may have a neck (not including the sealing ring) with an average width which may be an average diameter ranging for example between 1 and 3 mm or 3 and 7 mm or 7 and 8 mm or 8 and 16 mm. Optionally the neck may have a non-uniform cross section (for example an I beam and/or cross shaped cross section) and/or a tapered cross section.

For a non-uniform cross section, an average outer width may be defined as the width of the smallest oval that can enclose the neck averaged over the length of the neck. In some embodiments a fluid path between the extension and a reservoir cavity may include a 27 gauge needle or a needle ranging between 25 and 30 gauge or a needle ranging between 20 and 25 gauge or a needle ranging between 30 and 32 gauge. In some embodiments a needle protruding from an extension may include a 27 gauge needle or a needle ranging between 25 and 30 gauge or a needle ranging between 20 and 25 gauge or a needle ranging between 30 and 32 gauge.

It is expected that during the life of a patent maturing from this application many relevant technologies and/or materials will be developed and the scope of the terms are intended to include all such new technologies and materials a priori.

As used herein the terms "about", "approximately" and "substantially" refer to ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 7, from 1 to 5, from 2 to 7, from 2 to 6, from 3 to 6 etc., as well as individual numbers within that range, for example, 1, 2, 3, 7, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for shielding a needle of an injection device during removal from an injection site:
    a housing having a chassis and a mounting plate pivotably attached to the chassis;
    a base movably mounted to the chassis and including a contact surface having an adhesive for attachment to an injection zone;
    the needle being mounted on the mounting plate and a needle tip thereof being movable between an exposed position, wherein the needle tip projects outwardly from the housing, and a shielded position, wherein the needle tip is retracted within the housing;
    the mounting plate being movable between a first position, positioning the needle tip in the exposed position thereof, and a second position, positioning the needle tip in the shielded position thereof, in which the mounting plate is further distanced from said contact surface relative to the first position, and the base being movable between an extended position extended away from the chassis and a collapsed position collapsed against the chassis; and a lock operatively engaging the mounting plate in said first position of the mounting plate and said collapsed position of said base, inhibiting movement of said needle tip from the exposed position thereof to the shielded position thereof, wherein movement of said base from the collapsed position to the extended position disengages said lock from said mounting plate to allow movement of said needle tip from said exposed position to said shielded position.

2. The system of claim 1, wherein in said second position of the mounting plate, a center of mass of said housing is further from said contact surface than in said first position.

3. The system of claim 1, wherein said mounting plate is movable between said first position near said base and said second position distanced from said base.

4. The system of claim 1, further comprising a biasing member biasing said mounting plate toward said second position.

5. The system of claim 4, wherein said lock comprises a retainer that retains said mounting plate in said first position during drug delivery.

6. The system of claim 5, wherein said retainer is configured to release said mounting plate to said second position in response to pulling said housing away from said contact surface of said base.

7. The system of claim 6, wherein said chassis includes a second contact surface and a second adhesive such that when said contact surface of said base is attached to the injection zone and said mounting plate is in said first position, said second adhesive retains said mounting plate in said first position by adhesion.

8. The system of claim 7, wherein said second contact surface is flush to said contact surface of said base when said mounting plate is in said first position such that when said mounting plate is in said first position and said contact surface of said base is in contact with the injection site on a skin of a subject, said second contact surface is configured to also contact said skin of said subject.

9. The system of claim 7, wherein said housing is configured to encourage pulling said housing away from said injection zone from a position closer to said second contact surface than to said contact surface of said base.

10. The system of claim 1, further comprising an opening in said base and wherein said needle tip is aligned with said opening such that said needle tip passes through said opening when said needle tip moves from said exposed position to said shielded position.

11. The system of claim 10, wherein said needle tip is aligned with said opening both when said mounting plate is in said first position and when said mounting plate is in said second position.

12. The system of claim 1, further comprising a stored energy source and wherein said movement of said needle tip is powered by said stored energy source.

13. The system of claim 1, wherein said housing is shaped and sized for grasping by a human hand, such that grasping said housing and pulling it away from the contact surface causes said moving of said mounting plate from said first position to said second position.

* * * * *